United States Patent
Dong et al.

(10) Patent No.: US 7,019,114 B2
(45) Date of Patent: Mar. 28, 2006

(54) RECOMBINANT, BIOLOGICALLY ACTIVE HUMAN ZONA PELLUCIDA PROTEIN 3 (HZP3) TO TEST MALE FERTILITY

(75) Inventors: Ke-Wen Dong, Chesapeake, VA (US); Sergio Oehninger, Norfolk, VA (US); William E. Gibbons, Norfolk, VA (US)

(73) Assignee: Eastern Virginia Medical School, Norfolk, VA (US)

(*) Notice: Subject to any disclaimer, the term of this patent is extended or adjusted under 35 U.S.C. 154(b) by 0 days.

(21) Appl. No.: 09/252,828

(22) Filed: Feb. 19, 1999

(65) Prior Publication Data

US 2002/0172982 A1 Nov. 21, 2002

Related U.S. Application Data

(60) Provisional application No. 60/075,079, filed on Feb. 19, 1998.

(51) Int. Cl.
C07K 14/00 (2006.01)
C07K 1/00 (2006.01)

(52) U.S. Cl. ........................... 530/350; 530/827
(58) Field of Classification Search ............... 530/350, 530/827, 300, 326; 435/4, 7.1, 7.2, 7.6, 40.51, 435/183, 5, 6, 7, 290.1, 69.3, 253.1, 69.1, 435/240.2, 252.2, 252.3, 254.11, 320.1, 325, 435/235.1, 7.21; 436/65; 536/23.1, 27.1, 536/23.5, 24.1; 514/2, 13, 14, 21; 924/184.1, 924/204.1, 85.8, 88
See application file for complete search history.

(56) References Cited

U.S. PATENT DOCUMENTS

| | | | |
|---|---|---|---|
| 4,399,216 A | 8/1983 | Axel et al. | |
| 4,444,879 A | 4/1984 | Foster et al. | |
| 4,554,101 A | 11/1985 | Hopp | |
| 4,634,665 A | 1/1987 | Axel et al. | |
| 4,861,718 A | 8/1989 | Hirata et al. | |
| 4,889,803 A | 12/1989 | Revel et al. | |
| 4,960,704 A | 10/1990 | Ingolia et al. | |
| 5,034,322 A | 7/1991 | Rogers et al. | |
| 5,179,017 A | 1/1993 | Axel et al. | |
| 5,272,071 A | 12/1993 | Chappel | |
| 5,352,605 A | 10/1994 | Fraley et al. | |
| 5,618,698 A | 4/1997 | Lin | |
| 5,626,846 A * | 5/1997 | Dean | 424/184.1 |
| 5,641,487 A * | 6/1997 | Dean | 424/184.1 |
| 5,641,670 A | 6/1997 | Treco et al. | |
| 5,650,321 A | 7/1997 | Levy | |
| 5,672,488 A * | 9/1997 | Dean | 435/69.3 |
| 5,703,057 A | 12/1997 | Johnston et al. | |
| 5,710,038 A * | 1/1998 | Mes-Masson et al. | 435/240.2 |
| 5,766,924 A | 6/1998 | Levy | |
| 5,817,793 A | 10/1998 | Levy | |
| 5,821,350 A | 10/1998 | Huang et al. | |
| 5,837,497 A * | 11/1998 | Harris | 435/693 |

(Continued)

FOREIGN PATENT DOCUMENTS

| | | | |
|---|---|---|---|
| EP | 0488470 | | 5/1997 |
| WO | 90/15624 | | 12/1990 |
| WO | WO 92/03548 | * | 3/1992 |
| WO | 93/14786 | | 8/1993 |
| WO | 94/10304 | | 5/1994 |
| WO | WO 94/11019 | * | 5/1994 |
| WO | 94/22472 | | 10/1994 |
| WO | 95/27206 | | 10/1995 |
| WO | 96/05305 | | 2/1996 |
| WO | 96/06113 | | 2/1996 |
| WO | 98/37185 | | 8/1998 |
| WO | 99/34825 | | 7/1999 |
| WO | 99/42581 | | 8/1999 |
| WO | 99/52544 | | 10/1999 |
| WO | 99/64626 | | 12/1999 |
| WO | 99/64627 | | 12/1999 |
| WO | 99/65520 | | 12/1999 |
| WO | 99/65928 | | 12/1999 |

OTHER PUBLICATIONS

Kinloch, RA et al. Mapping the mouse ZP3 combining site for sperm by exon swapping and site-directed mutagenesis. Proc. Natl. Acad. Sci. USA 1995;92:263–267.*

Rosiere, TK & Wasserman, PM. Identification of a region of mouse zona pellucida glycoprotein mZP3 that possesses sperm receptor activity. Devel. Biol. 1992;154:309–317.*

Chamberlin et al., "Human homolog of the mouse sperm receptor." Proc. Natl. Acad. Sci. USA, Developmental Biology, vol. 87, pp. 6014–6018, Aug. 1990.*

Chamberlin et al., "Human homolog of the mouse receptor." Proc. Natl. Acad:Sci. USA., vol. 87, pp. 6014–6018, Aug. 1990, Developmental Biology.*

Ozgur et al., "Direct evidence for the involvement of carbohydrate sequences in humna sperm–zona pellucida binding.", Molecular Human Reproduction, vol. 4, No. 4, 1998, pp. 318–324.*

Chirgwin, John M., Alan E. Przybyla, Raymond J. MacDonald, and William J. Rutter. 1979. "Isolation of Biologically Active Ribonucleic Acid from Sources Enriched in Ribonuclease." *Biochemistry*, vol. 18, No. 24, pp. 5294–5299.

(Continued)

*Primary Examiner*—Robert A. Wax
*Assistant Examiner*—Suzanne M. Mayer
(74) *Attorney, Agent, or Firm*—Wilmer Cutler Pickering Hale and Dorr LLP

(57) ABSTRACT

The invention relates to methods for producing recombinant human zona pellucida protein ("rhZP3") and glycosylated peptide having biological activity of binding to human spermatozoa. A human ovarian cell line is used to produce rhZP3 having a glycosylation pattern required for full biological activity. Methods of determining useful peptides with binding activity for human sperm and their syntheses, as well as using such peptides and proteins in therapeutics and diagnostics are discussed.

9 Claims, 3 Drawing Sheets

U.S. PATENT DOCUMENTS

| | | | |
|---|---|---|---|
| 5,851,763 | A | 12/1998 | Heym et al. |
| 5,851,796 | A | 12/1998 | Schatz |
| 5,851,817 | A | 12/1998 | Hardy et al. |
| 5,869,053 | A * | 2/1999 | Stern et al. ............... 424/184.1 |
| 5,888,981 | A | 3/1999 | Bujard et al. |
| 5,891,718 | A | 4/1999 | Hobert et al. |
| 5,916,768 | A * | 6/1999 | Dean ......................... 435/69.3 |
| 5,922,927 | A | 7/1999 | Bujard et al. |
| 5,925,541 | A | 7/1999 | Goldstein et al. |
| 5,962,326 | A | 10/1999 | Shimada et al. |
| 5,968,773 | A | 10/1999 | Heddle et al. |
| 5,976,545 | A | 11/1999 | Harris et al. |
| 5,981,228 | A | 11/1999 | Harris et al. |
| 5,989,550 | A | 11/1999 | Harris et al. |
| 6,001,599 | A | 12/1999 | Harris et al. |
| 6,027,727 | A | 2/2000 | Harris et al. |
| 6,132,952 | A | 10/2000 | Cohen et al. |
| 6,264,953 | B1 | 7/2001 | Dunbar |
| 2002/0028470 | A1 | 3/2002 | Dong et al. |
| 2002/0172982 | A1 | 11/2002 | Dong et al. |
| 2003/0148930 | A1 | 8/2003 | Chi et al. |

OTHER PUBLICATIONS

Bleil, Jeffrey D. and Paul M. Wassarman. Jul. 1980. "Mammalian Sperm–Egg Interaction: Identification of a Glycoprotein in Mouse Egg Zonae Pellucidae Possessing Receptor Activity for Sperm." *Cell*. vol. 20, pp. 873–882.

Maggio, Edward T. 1980. *Enzyme–Immunoassay*. Boca Raton, FL: CRC Press, Inc. pp. 186–187.

Dunbar, Bonnie S., Cecilia Liu, and David W. Sammons. 1981. "Identification of the Three Major Proteins of Porcine and Rabbit Zonae Pellucidae by High Resolution Two–Dimensional Gel Electrophoresis: Comparison with Serum, Follicular Fluid, and Ovarian Cell Proteins." *Biology of Reproduction*. vol. 24, pp. 1111–1124.

McIlhinney, R. A. J. and Shashikant Patel. Mar. 1983. "Characterization of the Fibronectin Synthesized by Human Germ Cell Tumors." *Cancer Research*. vol. 43, pp. 1281–1288.

Florman, Harvey M. and Paul M. Wassarman. May 1985. O–Linked Oligosaccharides of Mouse Egg ZP3 Account for Its Sperm Receptor Activity. *Cell*. vol. 41, pp. 313–324.

Fukuda, Michiko N., Anne Dell, Jane E. Oates, and Minoru Fukuda. Jun. 1985. "Embryonal Lactosaminoglycan: The Structure of Branched Lactosaminoglycans with Novel Disialosyl (Sialyl alpha2→9 Sialyl) Terminals Isolated from PA1 Human Embryonal Carcinoma Cells." *The Journal of Biological Chemistry*. Vo. 260, No. 11, pp. 6623–6631.

Cross, Nicholas L., Patricio Morales, James W. Overstreet, and Frederick W. Hanson. May 1986. "Two Simple Methods for Detecting Acrosome–Reacted Human Sperm." *Gamete Research*. vol. 15, pp. 213–226.

Ringuette, Maurice J., Donna A. Sobieski, Steven M. Chamow, and Jurrien Dean. Jun. 1986. "Oocyte–Specific Gene Expression: Molecular Characterization of a cDNA Coding for ZP–3, the sperm Receptor of the Mouse Zona Pellucida." *Proc. Natl. Acad. Sci. USA*. vol. 83, pp. 4341–4345.

Burkman, Lani J., Charles C. Coddington, Daniel R. Franken, Thinus F. Kruger, Zev Rosenwaks, and Gary D. Hodgen. Apr. 1988. "The Hemizona Assay (HZA): Development of a Diagnostic Test for the Binding of Human Spermatozoa to the Human Hemizona Pellucida to Predict Fertilization Potential." *Fertility and Sterility*. vol. 49, No. 4, pp. 688–697.

Shabanowitz, R. B. and M. G. O'Rand. 1988. "Characterization of the Human Zona Pellucida from Fertilized and Unfertilized Eggs." *J. Reprod. Fert*. vol. 82, pp. 151–161.

Timmons, T. M. and B. S. Dunbar. 1988. "Antigens of Mammalian Zona Pellucida." *Perpectives in Immunoreproduction: Conception and Contraception*. New York: Hemisphere Publishing Co. pp. 242–260.

Wassarman, Paul M. 1988. "Zona Pellucida Glycoproteins." *Ann. Rev. Biochem*. vol. 57, pp. 415–442.

Saling, Patricia M. 1989. "Mammalian Sperm Interaction with Extracellular Matrices of the Egg." *Oxf. Rev. Reprod. Biol*. vol. 11, pp. 339–388.

Sambrook, J., E.F. Fritsch, and T. Maniatis. 1989. *Molecular Cloning: A Laboratory Manual*. $2^{nd}$ Edition. Cold Spring Harbor Laboratory Press. pp. 16.32–16.37.

Oehninger, Sergio, Anibal Acosta, and Gary D. Hodgen. Jan. 1990. "Antagonistic and Agonistic Properties of Saccharide Moieties in the Hemizona Assay." *Fertility and Sterility*. vol. 53, No. 1, pp. 143–149.

Furukawa, Tatsuhiko, Masayuki Ozawa, Ruo–Pan Huang, and Takashi Muramatsu. Mar. 1990. "A Heparin Binding Protein Whose Expression Increases During Differentiation of Embryonal Carcinoma Cells to Parietal Endoderm Cells: cDNA Cloning and Sequence Analysis." *J. Biochem*. vol. 108, No. 2, pp. 297–302.

Liang, Li–Fang, Steven M. Chamow, and Jurrien Dean. Apr. 1990. "Oocyte–Specific Expression of Mouse Zp–2: Developmental Regulation of the Zona Pellucida Genes." *Molecular and Cellular Biology*. vol. 10, No. 4, pp. 1507–1515.

Kinloch, Ross A., Betina Ruiz–Seiler, and Paul. M. Wassarman. Aug. 1990. "Genomic Organization and Polypeptide Primary Structure of Zona Pellucida Glycoprotein hZP3, the Hamster Sperm Receptor." *Developmental Biology*. vol. 142, pp. 414–421.

Wassarman, Paul M. 1990. "Profile of a Mammalian Sperm Receptor." *Development*. vol. 108, pp. 1–17.

Wassarman, P. M. 1990. "Regulation of Mammalian Fertilization by Zona Pellucida Glycoproteins." *J. Reprod. Fert., Suppl*. vol. 42, pp. 79–87.

1991. "Errata." *Developmental Biology*. vol. 145. pp. 203–204.

Saling, Patricia M. 1991. "How the Egg Regulates Sperm Function During Gamete Interaction: Facts and Fantasies." *Biology of Reproduction*. vol. 44, pp. 246–251.

Beebe, Stephen J., Lisette Leyton, Deborah Burks, Motoharu Ishikawa, Tom Fuerst, Jurrien Dean, and Patricia Saling. Jan. 1992. "Recombinant Mouse ZP3 Inhibits Sperm Binding and Induces the Acrosome Reaction." *Development Biology*. vol. 151, pp. 48–54.

Thillai–Koothan, P., Marcel Van Diun, and R. John Aitken. May 1993. "Cloning, Sequencing and Oocyte–Specific Expression of the Marmoset Sperm Receptor Protein, ZP3." *Zygote*. vol. 1, pp. 93–101.

Lee, Vaughan H., Eric Schwoebel, Sarvamangala Prasad, Peter Cheung, Therese M. Timmons, Richard Cook, and Bonnie S. Dunbar. Jun. 1993. "Identification and Structural Characterization of the 75–kDa Rabbit Zona Pellucida Protein," *The Journal of Biological Chemistry*. vol. 268, No. 17, pp. 12412–12417.

Liang, Li–Fang and Jurrien Dean. 1993. "Conservation of Mammalian Secondary Sperm Receptor Genes Enables the Promoter of the Human Gene to Function in Mouse Oocytes." *Developmental Biology*. vol. 156, pp. 399–408.

Varki, Ajit. 1993. "Biological Roles of Oligosaccharides: All of the Theories Are Correct." *Glycobiology*. vol. 3, No. 2, pp. 97–130.

Barratt, C.L.R., A. Whitmarsh, D.P. Hornby, S. Clements, L.D. Cooke, and H.D.M. Moore. 1994. "Glycosylation of Human Recombinant ZP3 Is Necessary to Induce the Human Acromsome Reaction" (Abstract No. 33). *Hum. Reprod*. vol. 9 (Suppl.).

Dunbar, B. S., S. Avery, V. Lee, S. Prasad, D. Schwahn, E. Schwoebel, S. Skinner, and B. Wilkins. 1994. "The Mammalian Zona Pellucida: Its Biochemistry, Immunochemistry, Molecular Biology, and Development Expression." *Reprod. Fertil. Dev*. vol. 6, pp. 331–347.

Hinsch, Klaus–Dieter, Elvira Hinsch, Burkhard Meinecke, Edda Töpfer–Petersen, Susanne Pfisterer, and Wolf–Bernhard Schill. 1994. "Identification of Mouse ZP3 Protein in Mammalian Oocytes with Antisera Against Synthetic ZP3 Peptides." *Biology of Reproduction*. vol. 51, pp. 193–204.

Van Duin, Marcel, Jan E.M. Polman, Ingeborg T.M. de Breet, Karin Van Ginneken, Hans Bunschoten, Arijan Grootenhuis, James Brindle, and R. John Aitken. 1994. "Recombinant Human Zona Pellucida Protein ZP3 Produced by Chinese Hamster Ovary Cells Induces the Human Sperm Acrosome Reaction and Promotes Sperm–Egg Fusion." *Biology of Reproduction*. vol. 51, pp. 607–617.

Varki, Ajit. 1994. "[2] Metabolic Radiolabeling of Glyconjugates." *Methods in Enzymology*. vol. 230, pp. 16–32.

Oehninger, Sergio, Charles C. Coddington, Gary D. Hodgen, and Markku Seppala. Feb. 1995. "Factors Affecting Fertilization: Endometrial Placental Protein 14 Reduces the Capacity Spermatozoa to Bind to the Human Zona Pellucida." *Fertility and Sterility*. vol. 63, No. 2, pp. 377–383.

Burks, D. J., R. Carballada, H. D. M. Moore, and P. M. Saling. Jul. 1995. "Interaction of a Tyrosine Kinase from Human Sperm with the Zona Pellucida at Fertilization." *Science*. vol. 269, pp. 83–86.

Barratt, Christopher L. R. and David P. Hornby. "Induction of the Human Acrosome Reaction by rhuZP3." 1995. *Human Sperm Acrosome Reaction*. Colloque INSERM/John Libbey Eurotext Ltd. vol. 236, pp. 105–122.

Lust, J.A., D.F. Jelinek, K.A. Donovan, L.A. Frederick, B.K. Huntley, J.K. Braaten, and N.J. Maihle. 1995. "Sequence, Expression and Function of an mRNA Encoding a Soluble Form of the Human Interleukin–6 Receptor (sIL–6R)." *Curr. Top. Microbiol. Immunol*. vol. 194, pp. 199–206.

Whitmarsh, A.J., M.J. Woolnough, H.D.M. Moore, D.P. Hornby, and C.L.R. Barratt, 1996, "Biological Activity of Recombinant Human ZP3 Produced in vitro: Potential for a Sperm Function Test." *Molecular Human Reproduction*. vol. 2, No. 12, pp. 911–919.

Franken, Daniel R., Patricio J. Morales, and Ursula F. Habenicht. Dec. 1996. "Inhibition of G Protein in Human Sperm and Its Influence on Acrosome Reaction and Zona Pellucida Binding." *Fertility and Sterility*. vol. 66, No. 6, pp. 1009–1011.

Brewis, I.A., R. Clayton, C.L.R. Barratt, D.P.J. Hornby, and H.D.M. Moore. 1996. "Recombinant Human Zona Pellucida Glycoprotein 3 Induces Calcium Influx and Acrosome Reaction in Human Spermatozoa." *Molecular Human Reproduction*. vol. 2, No. 8, pp. 583–589.

Chapman, Neil R. and Christopher L.R. Barratt. 1996. "The Role of Carbohydrate in Sperm–ZP3 Adhesion." *Molecular Human Reproduction*. vol. 2, No. 10, pp. 767–774.

Prasad, Sarvamangala V., Brendan Wilkins, Sheri M. Skinner, and Bonnie S. Dunbar. 1996. "Evaluating Zona Pellucida Structure and Function Using Antibodies to Rabbit 55 kDa ZP Protein Expressed in Baculovirus Expression System." *Molecular Reproduction and Development*. vol. 43, pp. 519–529.

Dong, Ke Wen, Ting Fung Chi, Yu Wen Juan, Chih Wei Chen, Zhiyong Lin, Xiao–Qin Xiang, Mary Mahony, William E. Gibbons, and Sergio Oehninger. Apr. 2001. "Characterization of the Biologic Activities of a Recombinant Human Zona Pellucida Protein 3 Expressed in Human Ovarian Tertocarcinoma (PA–1) Cells." *Am. J. Obstet. Gynecol*. pp. 835–844.

Bleil, Jeffrey A. et al., *Structure and Function of the Zona Pellucida: Identification and Characterization of the Proteins of the Mouse Oocyte's Zona Pellucida*, Dev. Biol. 76: pp. 185–202, (1980).

Saling, Patricia, *Mammalian Sperm interaction with extracellular matrices of the egg*, Oxford Reviews of Reproductive Biology, 11: pp. 339–388, (1989).

Saling, Patricia, *How the Egg Regulates Sperm Function during Garnete Interaction: Facts and Fantasies*, Biology of Reproduction, 44: pp. 246–251, (1991).

Kinloch, Ross A. et al, *Primary Structure of the mouse sperm receptor polypeptide determined by genomic cloning*, Proc. Natl. Sci., 85, pp. 6409–6413, (1988).

Beebe, Stephen J. et al., *Recombinant Mouse ZP3 Inhibits Sperm Binding and Induces the Acrosome Reaction*, Dev. Biol., 151: pp. 48–54, (1992).

Burkman, Lani, J., et al. *The hemizona assay (HZA): development of a diagnostic test for the binding of human spermatozoa to the human hemizona pellucida to predict fertilization potential*, Fertility and Sterility, 49: pp. 688–693, (1988).

Oehninger, S. et al., *Hermizona assay and its impact on the identification and treatment of human sperm dysfunctions*, Andrologia, 24: pp. 307–321, (1992).

Clark, Gary F. et al., *A role for glyconujugates in human development: the human feto–embryonic defence system hypothesis*, Human Reproduction, 11: pp. 467–473, (1996).

Barbosa, James A., *Site–Directed Mutagenesis of Class I HLA Genes: Role of Glycosylation in Surface Expression and Functional Recognition*, J. Exp. Med. 166: pp. 1329–1350 (1987).

Mansour, Suzanne L., *Disruption of the proto–oncogene int–2 in mouse embryo–derived stem cells: a general strategy for targeting mutations to non–selectable genes*, Nature, 336: pp. 348–349, (1988).

Bercegeay, S. et al. Composition of Human Zona Pellucida as Revealed by SDS–PAGE After Silver Staining. Molecular Reproduction and Development 41:355–359 (1995).

Bleil, Jeffrey D. et al. Sperm–Egg Interactions in the Mouse: Sequence of Events and Induction of the Acrosome Reaction by a Zone Pellucida Glycoprotein. Developmental Biology 95.317–324 (1988).

Bleil, Jeffrey D. et al. Identification of a Secondary Sperm Receptor in the Mouse Egg Zona Pellucida: Role in Maintenance of Binding of Acrosome–Reacted Sperm to Eggs. Developmental Biology 128.376–385 (1988).

Clark, Gary F. et al. New Concepts in Human Sperm–Zona Pellucida Interaction. Human Reproduction vol. 10 Supplement 1 (1995).

Duin, Marcel Van et al. Cloning and Characterization of the Human Sperm Receptor Ligand ZP3: Evidence for a Second Polymorphic Allele with a Different Frequency in the Causasian and Japanese Populations. Genomics 14, 1064–1070 (1992).

Duin, Marcel Van et al. Recombinant Human Zona Pellucida Protein ZP3 Produced by Chinese Hamster Ovary Cells Induces the Human Sperm Acrosome Reaction and Promotes Sperm–Egg Fusion. Biology of Reproduction 51, 607–617 (1994).

Greve, Jeffrey M. et al. Biosynthesis of the Major Zone Pellucida Glycoprotein Secreted by Ooctyes during Mammalian Oogenesis. Cell. vol. 31.749–759 Dec. (1982).

Gupta, S.K. et al. Immunoreactivity with Native Zona Pellucida of Antibodies against a 19 Amino Acid Symthetic Peptide Corresponding to Human ZP3. Journal of Reproductive Immunology 27:241–247, 1994).

Gupta, S.k. et al. Localization of Epitopes for Monoclonal Antibodies at the N–Terminus of the Porcine Zone Pellucida Glycoprotein pZPC. Molecular Reproduction and Development 42:220–225; (1995).

Harris, Jeffrey D. et al. Cloning and Characterization of Zona Pellucida Genes and cDNAs from a Variety of Mammalian Species: The ZPA, ZPB and ZPC Gene Families. The Journal of Sequencing and Mapping, vol. 4, pp. 361–393 (1994).

Kinloch, Roes A. et al. Embryonal Carcinoma Cells Transfected with ZP3 Genes Differentially Glycosylate Similar Polypeptides and Secrete Active Mouse Sperm Receptor. Rockefeller University Press, 0021–9525/91/11/655/10, (1991).

Kipersztok, Simon et al. POM–ZP3, a Bipartite Transcript Derived from Human ZP3 and a POM121 Homologue. Genomics 25, 354–359 (1995).

Litscher, Eveline S. et al. Recombinant Hamster Sperm Receptors that Exhibit Species–Specific Binding to Sperm. Zygote 4 (Aug.), pp229–236 (1996).

Liu, Chengyu et al. Zona Pellucida Glycoprotein mZP3 Bioactivity is not Dependent on the Extent of Glycosylation of its Polypeptide or on Sulfation and Sialylation of its Oligosaccharides. Journal of Cell Science 110.745–752 (1997).

Oehninger, Sergio et al. Use of a Specific Zona Pellucida (ZP) Protein 3 Antiserum as a Clinical Marker for Human ZP Integrity and Function. Fertility and Sterility vol. 65 No. 1, Jan. (1996).

Vazquez, Monica H. et al. Interaction of Mouse Sperm with Purified Sperm Receptors Covalently Linked to Silica Beads. Journal of Cell Science 92, 713–722 (1989).

Chapman et al.; "2. Sperm–zona Interaction and Recombinant DNA Technology"; Molecular Human Reproduction; vol. 3, No. 8; 1997; pp. 646–650.

Chen et al.; "Inactivation of the Mouse Sperm Receptor, mZP3, by Site–directed Mutagenesis of Individual Serine Residues Located at the Combining site for Sperm"; Proc. Natl. Acad. Sci. USA; vol. 95; May 1998; pp. 6193–6197.

Hansen et al.; "O–Glycbase Version 2.0: a Revised database of O–glycosylated Proteins"; Nucleic Acids Research; vol. 25, No. 1; 1997; pp. 178–282.

Hansen et al.; "NetOglyc: Prediction of Mucin Type O–glycosylation Sites Based on Sequence Context and Surface Accessibility"; Glycoconjugate Journal; 1998; pp 115–130.

Van Duin et al.; "recombinant Human Zona Pellucida Protein ZP3 Produced by Chinese Hamster Ovary Cells Induces the Human Sperm Acrosome Reaction and Promotes Sperm–Egg Fusion"; Biology of Reproduction; vol. 51; 1994; pp. 607–617.

Clark et al.; "Role for Glycoconjugates in Cellular Communication in the Human Reproductive System"; Molecular Human Reproduction; vol. 2, No. 7; 1996; pp. 513–517.

Patankar et al.; "Expression of Glycans Linked to Natural Killer Cell Inhibition of the Human Zona Pellucida"; Molecular Human Reproduction; vol. 3, No. 6; 1997; pp. 501–505.

Ozgur et al.; "Direct Evidence for the Involvement of Carbohydrate Sequences in Human Sperm–zona Pellucida Binding"; Molecular Human Reproduction; vol. 4, No. 4; 1998; pp. 318–324.

Chamberlin et al.; "Human Homolog of the Mouse Sperm Receptor"; Proc. Natl. Acad. Sci. USA; vol. 87, Aug. 1990; pp. 6014–6018.

Kinloch et al.; "Mapping the Mouse ZP3 Combining Site For Sperm By Exon Swapping and Site–directed Mutagenesis"; Proceedings of the National Academy of Sciences of USA; vol. 92; Jan. 1995; pp. 263–267; XP–002108572.

Chamberlin et al.; "Human Homolog of the Mouse Sperm Receptor"; Proceedings of the National Academy of Sciences of USA; vol. 87; Aug. 1990; pp. 6014–6018; XP–00210857.

Van Duin et al.; "Cloning and Characterization of the Human Sperm Receptor Ligand ZP3: Evidence of A Second Polamorphic Allele With Different Frequency in the Causasian and the Japanese Populations"; Genomics; vol. 14, No. 4; Dec. 1992; pp. 1064–1070; XP–002108574.

Bagavant et al.; "Immunogenicity and Contraceptive Potential of A Zone Pellucida 3 Peptide Vaccine"; Biology of Reproduction; vol. 56, No. 3; Mar. 1997; pp. 764–770; XP–002108575.

Harrison, R. G. May 25–27, 1960. "Proceedings of the Society for the Study of Fertility," *Annual Conference.* London.

Hartmann, John F. et al. Oct. 1972. "Early Contact Interactions Between Mammalian Gametes *In Vitro*: Evidence That the Vitellus Influences Adherence Between Sperm and Zona Pellucida," *Proc. Nat. Acad. Sci. USA*, vol. 69, No. 10, pp. 2767–2769.

O'Farrell, Patrick H. May 25, 1975. "High Resolution Two–Dimensional Electrophoresis of Proteins." *The Journal of Biological Chemistry*, vol. 250, No. 10, pp. 4007–4021.

Russell, Lonnie et al. Jul. 1979. "Morphologic Characteristics of the Chemically Induced Acrosome Reaction in Human Spermatozoa." *Fertility and Sterility*, vol. 32, No. 1, pp. 87–92.

Sailing, Patricia M. et al. 1979. "An Ultrastructural Study of Epididymal Mouse Spermatozoa Binding to Zonae Pellucidae in Vitro: Sequential Relationship to the Acrosome Reaction." *J. Exp. Zool.*vol. 209, pp. 229–238.

Hook, Ernest B. Sep. 1981. "Rates of Chromosomes Abnormalities at Different Maternal Ages." *Obstetrics and Gynecology*, vol. 58, No. 3, pp. 282–285.

Koehler, James K. 1981. "Surface Alterations During the Capacitation of Mammalian Spermatozoa." *American Journal of Primatology*. vol. 1, pp. 131–141.

Yanagimachi, R. 1981. "Mechanisms of fertilization in mammals", In Mastroianni L Jr and Biggers JD (eds): *Fertilization and Embryonic Development In Vitro*. New York, Plenum Press, pp. 81–182.

Yanagimachi, Ryuzo et al. 1981. "Sperm Autoantigens and Fertilization: II. Effects of Anti–Guinea Pig Sperm Autoantibodies on Sperm–Ovum Interactions." *Biology of Reproduction*. vol. 24, pp. 512–518.

Ficsor, Gyula et al. Apr. 1983. "Gelatin–Substrate Film Technique for Detection of Acrosin in Single Mammalian Sperm." *Fertility and Sterility*. vol. 39, No. 4, pp. 548–552.

Mack, S. et al. 1983. "Acrosomal Enzymes of Human Spermatozoa Before and After In Vitro Capacitation." *Biology of Reproduction*. vol. 28, pp. 1032–1042.

Hyne, R. V. et al. 1984. "Sodium Requirement for Capacitation and Membrane Fusion During the Guinea–Pig Sperm Acrosome Reaction." *J. Reprod. Fert.*vol. 70, pp. 83–94.

Ward, Cynthia R. and Bayard T. Storey. 1984. "Determination of the Time Course of Capacitation in Mouse Spermatozoa Using a Chloretracycline Fluorescence Assay." *Developmental Biology*. vol. 104, pp. 287–296.

Bleil, Jeffrey D. and Paul M. Wassarman. Apr. 1986. "Autoradiographic Visualization of the Mouse Egg's Sperm Receptor Bound to Sperm." *The Journal of Cel l Biology*. vol. 102, pp. 1363–1371.

Menken, Jane et al. Sep. 26, 1986. "Age and Infertility." *Science*. vol. 233, pp. 1389–1394.

Fournier–Delpech, Suzanne and Michel Courot. 1987. "Sperm –Zona Pellucida Binding Activity." *Oxford Review of Reproductive Biology*. vol. 9, pp. 294–300

Lee, Michael A. et al. Oct. 1987. "Capacitation and Acrosome Reactions in Humans Spermatozoa Monitored by a Chloretracycline Fluorescence Assay." *Fertility and Sterility*. vol. 48, No. 4, pp. 649–658.

Timmons, T. M. et al. 1987. "Use of Specific Monoclonal and Polyclonal Antibodies to Define Distinct Antigens of the Porcine Zonae Pellucidae." *Biology of Reproduction*. vol. 36, pp. 1275–1287.

Bleil, Jeffrey D. and Paul M. Wassarman. Sep. 1988. "Galactose at the Nonreducing Terminus of O–Linked Oligosaccharides of Mouse Egg Zona Pellucida Glycoprotein ZP3 Is Essential for the Glycoprotein's Sperm Receptor Activity." *Proc. Natl. Acad. Sci. USA*. vol. 85, pp. 6778–3782.

Conover, JC and Gwatkin, RB. Jul. 1988. "Fertilization of zona–drilled mouse oocytes treated with a monoclonal antibody to the zonal glycoprotein, ZP3." *J. Exp. Zool*.vol. 247, No. 1, pp. 113–8.

Shabanowitz, RB and O'RAND, MG. 1988. "molecular changes in the human zona pellucida associated with fertilization and human sperm–zona interactions." *Ann. N.Y. Acad. Sci*.vol. 541, pp. 621–32.

Cross, Nicholas L. et al. 1988. "Induction of Acrosome Reactions by the Human Zona Pellucida." *Biology of Reproduction*. vol. 38, pp. 235–244.

Liu, De Yi et al. Nov. 1988. "A Human Sperm–Zona Pellucida Binding Test Using Oocytes That Failed to Fertilize In Vitro." *Fertility and Sterility*. vol. 50, No. 5, pp. 782–788.

Macek, Mary Beth and Barry D. Shur. 1988. "Protein–Carbohydrate Complementarity in Mammalian Gamete Recognition." *Gamete Research*. vol. 20, pp. 93–109.

Kennedy, W.P. et al. May/Jun. 1989. "A Simple, Clinical Assay to Evaluate the Acrosin Activity of Human Spermatozoa." *Journal of Andrology*. vol. 10, No. 3, pp. 221–231.

Leyton, Lisette and Patricia Saling. Jun. 1989. "Evidence That Aggregation of Mouse Sperm Receptors by ZP3 Triggers the Acrosome Reaction." *The Journal of Cell Biology*. vol. 108, pp. 2163–5168.

Jones, R. 1990. "Identification and Functions of Mammalian Sperm–Egg Recognition Molecules During Fertilization." *J. Reprod. Fert. Suppl*.vol. 42, pp. 89–105.

Von–Bernhardt, R. et al. Jan.–Feb. 1990. "Round–headed spermatozoa; a model to study the role of the acrosome in early events of gamete interaction." *Andrologia*. vol. 22, No. 1, pp. 12–20.

Shabanowitz, RB. Aug. 1990. "Mouse antibodies to human zona pellucida: evidence that human ZP3 is strongly immunogenic and contains two distinct isomer chains." *Biol. Rprod*.vol. 43, No. 2, pp. 260–70.

Kopf. G. S. 1990. "Zonal Pellucida–Mediated Signal Transaction in Mammalian Spermatozoa." *J. Reprod. Fert., Suppl*.vol. 42, pp. 33–49.

Topfer–Petersen E. et al. 1990. "Cell biology of acrosomal proteins." *Andrologia*; vol. 22, No. 1, pp. 110–21.

Naz, RK et al. May 1991, "Role of membrane phosphotyrosine protein in human spermatozoal function." *J. Cell Sci*.vol. 99, No. 1, pp. 157–65.

Koyama, K. et al. Nov. 1991. "Blocking of human sperm–zona interaction by monoclonal antibodies to a glycoprotein family (ZP4) of porcine zona pellucia." *Biol. Reprod*. vol. 45, No. 5, pp. 727–35.

Yurewicz, EC et al. Oct. 1991. "Isolation, composition, and biological activity of sugar chains of porcine oocyte zona pellucida 55K glycoproteins." *Mol. Reprod. Dev*.vol. 30, No. 2, pp. 126–34.

Millar, SE et al. Dec. 1991. "Oocyte–specific factors bind a conserved upstream sequence required for mouse zona pellucida promoter activity." *Mol. Cell. Biol*.vol. 11, No. 12, pp. 6197–204.

Keenan, JA et al. Jan. 1991. "Endocrine response in rabbits immunized with native versus deglycosylated porcine zonalpellucida antigens." *Biol. Reprod*.vol. 44, No. 1, pp. 150–6.

Naz, RK et al. May 1991. "Human spermatozoal FA–1 with ZP3 of porcine zona pellucida." *J. Reprod. Immunol*.vol. 20, No. 1, pp. 43–58.

Hasegawa, A. Feb. 1991. "Isolation of four major glycoprotein families (ZP1, ZP2, ZP3, ZP4) of porcine zona pellucida and characterization of antisera raised to each glycoprotein family." *Nippon Sanka Fujinka Gakkni Zasshi*. vol. 43, No. 2, pp. 221–6.

Oehninger, Sergio et al. Jan. 1991. "Nature of the Inhibitory Effect of Complex Saccharide Moieties on the Tight Binding Human Spermatozoa to the Human Zona Pellucida." *Fertility and Sterility*. vol. 55, No. 1, pp. 165–169.

Schowebel, Eric et al., Apr. 15, 1991. "Isolation and Characterization of a Full–Length cDNA Encoding the 55–kDa Rabbit Zona Pellucida Protein." *The Journal of Biological Chemistry*. vol. 266, No. 11, pp. 7214–7219.

Oehninger, Sergio et al. May 1991. "Recurrent Failure of In Vitro Fertilization: Role of the Hemizona Assay in the Sequential Diagnosis of Specific Sperm–Oocyte Defects." *Am. J. Obstet. Gynecol*.vol. 164, pp. 1210–1215.

Aarons, David et al. 1991. "Aerosome Reaction Induced by Immunoaggregation of a Proteinase Inhibitor Bound to the Murine Sperm Head." *Molecular Reproduction and Development*. vol. 30, pp. 258–264.

Macek, Mary Beth et al. 1991. "Aggregation of β–1 4–Galactosyltransferase on Mouse Sperm Induces the Acrosome Reaction."*Developmental Biology*. vol. 147, pp. 440–444.

Mortillo, Steven and Paul M. Wasarman. 1991. "Differential Binding of Gold–Labeled Zona Pellucida Glycoproteins mZP2 and mZP3 to Mouse Sperm Membrane Compartments." *Development*. vol. 113, pp. 141–149.

Wassarman, Paul M. and Steven Mortillo. 1991. "Structure of the Mouse Egg Extracellular Coat, the Zona Pellucida." *International Review of Cytology*. vol. 130, pp. 85–97.

Dean, Jurrien. Apr. 1992. "Biology of Mammalian Fertilization: Role of the Zona Pellucida." *The Journal of Clinical Investigation, Inc.*. vol. 89, pp. 1055–1059.

Oehninger, Sergio. 1992. "Diagnostic Significance of Sperm–Zona Pellucida." *Reproductive Medicine Review*, vol. 1, pp. 57–81.

Frasher, Douglas C. et al. 1992. "Primary Structure of the *Aequorea Victoria*Green–Fluorescent Protein.". *Gene*. vol. 111, pp. 229–233.

Rosiere, Thomas K. and Paul M. Wassarman. 1992. "Identification of a Region of Mouse Zona Pellucida Glycoprotein mZP3 That Possesses Sperm Receptor Activity." *Developmental Biology*. vol. 154, pp. 309–317.

Salzberger, Z. et al. 1992. "Loss of Acid Phosphatase from Rat Spermatozoa as Method for Assessing the Acrosome Reaction." *Andrologia*. vol. 24, pp. 155–159.

Rhim, SH et al. Jan. 1992. "Autoimmune disease of the ovary induced by a ZP3 peptide from the mouse zona pellucida." *J. Clin. Invest.*vol. 89, No. 1, pp. 28–35.

Yurewicz,,BC et al. Oct. 1992. "Porcine oocyte zona pellucida M(r) 55,000 glycoproteins: identification of O–glycosylated domains." *Mol. Reprod. Dev.*vol. 33, No. 2, pp. 182–8.

Patterson, M. et al. Apr. 1992. "Analysis of the contraceptive potential of antibodies against native and deglycosylated porcine ZP3 in vivo and in vitro." *Biol. Reprod.*vol. 46, No. 4, pp. 523–34.

Tulsiani, DR et al. Jan. 1992. "Evidence for the presence of high–mannose/hybrid oligosaccharide chain(s) on the mouse ZP2 and ZP3." *Biol. Reprod.*vol. 46, No. 1, pp. 93–100.

Bagavant, H. et al. Dec. 1993. "Block in porcine gamete interaction by polyclonal antibodies to a pig ZP3 beta fragment having partial sequence homology to human ZP3." *J. Reprod. Immunol.*vol. 25, No. 3, pp. 277–83.

Toner, James P. and Jill Taylor Flood. Jun. 1993. "Fertility After the Age of 40." *Perimenopausal Health Care*. vol. 29, No. 2, pp. 261–272.

Patankar, Manish S. et al. Oct. 15, 1993. "A Revised Structure for Fucoidan May Explain Some of Its Biological Activities. " *The Journal of Biological Chemistry*. vol. 268, No. 29, pp. 21770–21776.

Oehninger, Sergio et al. 1993. "The Specificity of Human Spermatozoa/Zona Pellucida Interaction Under Hemizona Assay Conditions." *Molecular Reproduction and Development*. vol. 35, pp. 57–61.

Yurewicz, Edward C. et al. 1993. "Porcine Zona Pellucida ZP3αGlycoprotein Mediates Binding of the Biotin–Labeled $M_r$ 55,000 Family (ZP3) to Boar Sperm Membrane Vesicles." *Molecular Reproduction and Development*. vol. 36, pp. 382–389.

Yurewicz, EC et al. May 1993. "Generation and characterization of site–directed antisera against an amino–terminal segment of a 55 kDa sperm adhesive glycoprotein from zona pellucida of pig oocytes." *J. Reprod. Fertil.*vol. 98, No. 1, pp. 147–152.

Yurewicz, EC et al. Aug. 1993. "Nucleotide sequence of cDNA encoding ZP3 alpha, a sperm–binding glcoprotein from zona pellucida of pig oocyte." *Biochim. Biophys. Acta*. vol. 1174, No. 2, pp. 211–4.

Van Duin, M. et al. 1993. "The human gene for zona pellucida glycoprotein ZP3 and a second polymorphic locus are located on chromosome 7." *Cytogenet. Cell. Genet*. vol. 63, No. 2, pp. 111–3.

Chalfie, M . et al. Feb. 1994. "Green fluorescent protein as a marker for gene expression." *Science*. vol. 263, No. 5148, pp. 802–5.

Wang, Shengxian and Tulle Hazelrigg. Jun. 2, 1994. "Implications for bcd mRNA Localization from Spatial Distribution of exu Protein in *Drosophila*Oogenesis."*Nature*. vol. 369, pp. 400–403.

Arts, Eugene G. J. M. et al. Nov. 1994. "A New Method to Detect Acrosome–Reacted Spermatozoa Using Biotinylated Soybean Trypsin Inhibitor." *Fertility and Sterility*. vol. 62, No. 5, pp. 1044–1055.

Bielfeld, Peter et al. Dec. 1994. "Are Capacitation or Calcium Ion Influx Required for the Human Sperm Acrosome Reaction?"*Fertility and Sterility*. vol. 62, No. 6, pp. 1255–1261.

Flach, Jean et al. Dec. 1994. "A Yeast RNA–Binding Protein Shuttles Between the Nucleus and the Cytoplasm." *Molecular and Cellular Biology*. vol. 14, No. 12, pp. 8399–8407.

Inouye, Satoshi and Frederick L. Tsuji. 1994. "Evidence for Redox Forms of the Aequorea Green Fluorescent Protein." *FEBS Letters*. vol. 351, pp. 211–214.

Naz, RK et al. Dec. 1994. "Molecular identities of human sperm proteins that bind human zona pellucida: nature of sperm–zona interaction, tyrosine kinase activity, and the involvement of FA–1." *Mol. Reprod. Dev.*vol. 39, No. 4, pp. 397–408.

Bagavant, H. et al., Sep. 1994. "Antifertility effects of porcine zona pellucida–3 immunization using permissible adjuvants in female bonnet monkeys (Macaca radiato): reversibility, effect on follicular development and hormonal profiles." *J. Reprod. Fert.*, vol. 102, No. 1, pp. 17–25.

Hinsch, KD et al. Oct. 1994. "Anti–ZP3 antibodies binding to the human zona pellucida: effect of oocyte–storage conditions." *Am. J. Reprod. Immunol.*vol. 32, No. 3, pp. 146–51.

Wydner, KS et al., Sep. 1994. "Use of an intron polymorphism to localize the tropoelastin gene to mouse chromosome 5 in a region of linkage conservation with human chromosome 7." *Genomics*. vol. 23, No. 1, pp. 125–31.

Cui, KH et al. Jan. 1994. "Sex determination of preimplantation embryos by human testis–determining gene amplification." *Lancet*. vol. 343, No. 8889, pp. 79–82.

Crozet, N. May 1994. "Acrosome reaction and fertilization." *Contracept. Fertil. Sex*. vol. 22, No. 5, pp. 328–30.

Marshall, John et al. Feb. 1995. "The Jellyfish Green Fluorescent Protein: A New Tool for Studying Ion Channel Expression and Function." *Neuron*. vol. 14, pp. 211–215.

Henkel, Ralf et al. May/Jun. 1995. "Acrosin Activity of Human Spermatozoa by Means of a Simple Gelatinolytic Technique: A Method Useful for IVF." *Journal of Andrology*. vol. 16, No. 3, pp. 272–277.

Epifano, O. et al..Nov. 1995. "Mouse ZP1 encodes a zona pellucida proteins homologous to egg envelope protein in mammals and fish." *J. Biol. Chem.*vol. 270, No. 45, pp. 27254–8.

Lou, YH et al. Oct. 1995. "Altered target organ. A mechanism of postrecovery resistance to murine autoimmune oophoritis." *J. Immunol.*vol. 155, No. 7, pp. 3667–73.

Aitken, RJ et al. May 1995. "Redox regulation of tyrosine phosphorylation in human spermatozoa and its role in the control of human sperm function." *J. Cell Sci.*vol. 108, No. 5, pp. 2017–25.

Nata, K. et al. Jun. 1995. "The structure of the Aplysia kurodai gene encoding ADP–ribosyl cyclase, a second–messenger enzyme." *Gene*. vol. 158, No. 2, pp. 213–8.

Perry, Raquel L. et al. Jul. 1995. "A Time Course Study of Capacitation and the Acrosome Reaction in Human Spermatozoa Using a Revised Chlortetracycline Pattern Classification." *Fertility and Sterility*. vol. 64, No. 1, pp. 150–159.

Dell, Anne et al. Oct. 13, 1995. "Structural Analysis of the Oligosaccharides Derived from Glycodelin, a Human Glycoprotein with Potent Immunosuppressive and Contraceptive Activities." *The Journal of Biological Chemistry*. vol. 270, No. 41, pp. 24116–24126.

Kolluri, SK et al. 1995. "Nucleotide sequence of cDNA encoding a bonnet monkey (Macaca radiata) zona pellucida glycoprotein–ZP3." *Reprod. Fert. Dev.*vol. 7, No. 5, pp. 1209–12.

MacKenna, A. 1995. "Contribution of the Male Factor to Unexplained Infertility: A Review." *International Journal of Andrology*. vol. 18, Suppl. 1, pp. 58–61.

Stearns, Tim. 1995. "The Green Revolution: Green Fluorescent Protein Allows Gene Expression and Protein Localization to be Observed in Living Cells." *Current Biology*. vol. 5, No. 3, pp. 262–264.

Wassarman, Paul M. and Eveline S. Litscher. 1995. "Sperm–Egg Recognition Mechanisms in Mammals." *Current Topics in Development Biology*. vol. 30, pp. 1–19.

Cheng, Feng–Fang et al. Nov./Dec. 1996. "Use of Peanut Agglutinin to Assess the Acrosomal Status and Zona Pellucida–Induced Acrosome Reaction in Stallion Spermatozoa." *Journal of Andrology*. vol. 17, No. 6, pp. 674–682.

Morris, Howard R. et al. Dec. 13, 1996. "Gender–Specific Glycosylation of Human Glycodelin Affects in Contraceptive Activity." *The Journal of Biological Chemistry*. vol. 271, No. 50, pp. 32159–32167.

Barros, C. et al. 1996. "Early Steps of Sperm–Egg Interactions During Mammalian Fertilization." *Cell Biology International*. vol. 20, No. 1, pp. 33–39.

Bruch, J. et al. 1996. "Mapping of type I loci from human chromosome 7 reveals segments of conserved synteny on pig chromosomes 3,9, and 18." *Cytogenet. Cell. Genet*. vol. 73, No. 3, pp. 164–67

Liu, De Yi and H. W. Gordon Baker. 1996. "A Simple Method for Assessment of the Human Acrosome Reaction of Spermatozoa Bound to the Zona Pellucida: Lack of Relationship With Ionophore A23187–Induced Acrosome Reaction." *Human Reproduction*. vol. 11, No. 3, pp. 551–557.

Mortimer, David and Lynn Fraser. 1996. "Consensus Workshop on Advanced Diagnostic Andrology Techniques: ESHRE Andrology Special Interest Group." *Human Reproduction*. vol. 11, No. 7, pp. 1463–1479.

Oehninger, Sergio et al. Mar. 1997. "Approaching the Next Millennium: How Should We Manage Andrology Diagnosis in the Intracytoplasmic Sperm Injection Era?" *Fertility and Sterility*. vol. 67, No. 3, pp. 434–436.

Oehninger, Sergio et al. Jun. 1977. "Clinical Significance of Human Sperm–Zona Pellucida Binding." *Fertility and Sterility*. vol. 67, No. 6, pp. 1121–1127.

Carver–Ward, J. A. et al. 1997. "Genetics: Comparative Flow Cytometric Analysis of the Human Sperm Acrosome Reaction Using CD46 Antibody and Lectins." *Journal of Assisted Reproduction and Genetics*. vol. 14, No. 2, pp. 111–119.

Franken, D. R. et al. 1997. "Zona Pellucida Mediated Acrosome Reaction and Sperm Morphology." *Andrologia*. vol. 29, pp. 311–317.

Kohn, F.M. et al., 1997. "Detection of Human Acrosome Reaction: Comparison Between Methods Uisng Double Staining, *Pisum Sativum*Agglutinin, Concanavalin A and Transmission Electron Microscopy." *Human Reproduction*. vol. 12, No. 4, pp. 714–721.

Margalit, I. et al. 1997. "A Novel Method for Evaluating the Acrosomal Status of Mammalian Spermatozoa."*Archives of Andrology*. vol. 38, pp. 87–99.

Mortensen, Richard et al. 1997. "Selection of Transfected Mammalian Cells."*Current Protocols in Molecular Biology*. pp. 9.5.1–9.5.6.

Shalgi, R. and T. Raz. "The Role of Carbohydrate Residues in Mammalian Fertilization." *Histol Histopathol.*vol. 12, pp. 813–822.

Arkin, Shy. Feb. 20, 1998. "Protein Glycosylation."www-.bio.cam.ac.uk/–sa232/tex/MVSTIA_4–8_Shy/node13.html. Printed Feb. 4, 1999.

Hansen, Jan. Aug. 4, 1998. "NetOGlyc 2.0 Prediction Server: Center for Biological Sequence Analysis." www.cbs.dtu.dk/services/NetOGlyc/. Printed Feb. 4, 1999.

Chuang, Alex T. and Stuart S. Howards. Nov. 1998. "Male Infertility: Evaluation and Nonsurgical Therapy." *Office Management of Urologic Problems*. vol. 24, No. 4, pp. 703–713.

Greenhouse, Stephen et al. 1998. "Insights from Model Systems: Genetic Causes of Female Infertility: Targeted Mutagenesis in Mice."*Am. J. Hum. Genet*. vol. 62, pp. 1282–1287.

Hansen, Jan E. et al. 1998. "NetOglyc: Prediction of Mucin Type O–Glycosylation Sites Based on Sequence Context and Surface Accessibility." *Glyconjugate Journal*. vol. 15, pp. 115–130.

Henkel, R. et al. 1998. "Zona Pellucida as Physiological Trigger for the Induction of Acrosome Reaction."*Adrologia*. vol. 30, pp. 275–280.

Irvine, D. S. "Epidemiology and aetiology of male infertility," *Human Reprod.*vol. 13, No. 1, pp. 33–44.

Oehninger, S. et al. 1998. "Involvement of Selectin–Like Carbohydrate Binding Specificity in Human Gamete Interaction." *Andrologia*. vol. 30, pp. 269–274.

Jaiswal, B.S. et al. 1999. "Detection of Partial and Complete Acrosome Reaction in Human Spermatozoa: Which Inducers and Probes to Use?" *Molecular Human Reproduction*. vol. 5, No. 3, pp. 214–219.

Tsubamoto, H. et al. 1999. "Expression of recombinant human zonal pellucida protein 2 and its binding capacity to spermatozoa." *Biol. Reprod.*vol. 61, pp. 1649–54.

Dean, Jurien. Jun. 24, 2000. "Maternal Effects on Flliculogenesis, Fertilization and Early Development." *Program & Abstracts: The Endocrine Society's 82nd Annual Meeting*. Oocyte Development Symposium Session.

Latif. R. and P. Graves. 2000. "Techniques in Thyroidology: Fluorescent Probes: Looking Backward and Looking Forward." *Thyroid*. vol. 10, No. 5.

Patra, Ashok K. et al. 2000. "Refolding'Structural Transition and Spermatozoa–Binding of Recombinant Bonnet Monkey (*Macaca Radiata*Zona Pellucida Glycoprotein–C Expressed in *Escherichia coli*". *Eur. J. Biochem*. vol. 267, pp. 7075–7081.

Dong, Ke Wen et al. 2001. "Characterization of the Biologic Activities of Recombinant Human Zona Pellucida Protein 3 Expressed in Human Ovarian Tetratocarcinoma (PA–1) Cells." *Am J. Obstet. Gynecol*.vol. 184, pp. 835–844.

Pietrobon, Elisa O. et al. Jan./Feb. 2001. "Detection of the Mouse Acrosome Reaction by Acid Phosphatase. Comparison With Chlortetracycline and Electron Microscopy." *Journal of Andrology*. vol. 22, No. 1, pp. 96–103.

Esterhuizen, A.D. et al. 2001. "Clinical Importance of Zona Pellucida–Induced Aerosome Reaction and Its Predictive Value for IVF." *Human Reproduction*. vol. 16, No. 1, pp. 138–144.

Zhao, Ming et al. May 2002. "Conserved Furin Cleavage Site Not Essential for Secretion and Integration of ZP3 into the Extracellular Egg Coat of Transgenic Mice." *Molecular and Cellular Biology*. vol. 22, No. 9, pp. 3111–3120.

Mar. 21, 2005. Communication from European Patent Office recording EP 02753427.0.

Kinloch, Ross A. et al. 1989. "Profile of a Mammalian Sperm Receptor Gene." *The New Biologist*. vol. 1, No. 3, pp. 232–238.

Oehninger, Sergio et al. 1992. "Male Infertility: The Impact of Assisted Reproductive Technologies." *Current Opinion in Obstetrics and Gynecology*. 4; 185–196.

\* cited by examiner

Figure 1

Ser Trp Phe Pro Val Glu Gly Pro Ala Asp Ile Cys Gln Cys Cys Asn Lys Gly Asp Cys Gly
308                              318                             328

Thr Pro Ser His Ser Arg Arg Gln Pro His Val Met Ser Gln Trp Ser Arg Ser Ala Ser (SEQ ID NO: 2)
                              338                             348

Figure 2

Name: HUMAN        Length:   41
SWFPVEGPADICQCCNKGDCGTPSHSRRQPHVMSQWSRSAS        (SEQ ID NO: 2)
. . . . . . . . . . . . . . . . . . . . . . . . . . . . . . . . . . . . . .

| Name  | Residue | No. | Potential | Threshold | Assignment |
|-------|---------|-----|-----------|-----------|------------|
| HUMAN | Thr     | 22  | 0.0285    | 0.4982    |            |

| Name  | Residue | No. | Potential | Threshold | Assignment |
|-------|---------|-----|-----------|-----------|------------|
| HUMAN | Ser     | 1   | 0.0629    | 0.5132    |            |
| HUMAN | Ser     | 24  | 0.0104    | 0.5253    |            |
| HUMAN | Ser     | 26  | 0.0265    | 0.5309    |            |
| HUMAN | Ser     | 34  | 0.0033    | 0.6267    |            |
| HUMAN | Ser     | 37  | 0.4498    | 0.5825    |            |
| HUMAN | Ser     | 39  | 0.0009    | 0.5126    |            |
| HUMAN | Ser     | 41  | 0.0082    | 0.5022    |            |

Figure 3

Name: MOUSE Length: 41
SWLPVQGDADICDCCSHGNCSNSSSSQFQIHGPRQWSKLVS (SEQ ID NO: 3)
. . . . . . . . . . . . . . . . . . . . . . . . . . . . . . . . . . . . . . . .

| Name | Residue | No. | Potential | Threshold | Assignment |
|------|---------|-----|-----------|-----------|------------|
| Name | Residue | No. | Potential | Threshold | Assignment |
| MOUSE | Ser | 1 | 0.0116 | 0.5078 | |
| MOUSE | Ser | 16 | 0.0002 | 0.5747 | |
| MOUSE | Ser | 21 | 0.0403 | 0.5845 | |
| MOUSE | Ser | 23 | 0.0074 | 0.5310 | |
| MOUSE | Ser | 24 | 0.1625 | 0.5397 | |
| MOUSE | Ser | 25 | 0.0167 | 0.5585 | |
| MOUSE | Ser | 26 | 0.0003 | 0.5656 | |
| MOUSE | Ser | 37 | 0.0024 | 0.5627 | |
| MOUSE | Ser | 41 | 0.0005 | 0.5127 | |

RECOMBINANT, BIOLOGICALLY ACTIVE HUMAN ZONA PELLUCIDA PROTEIN 3 (HZP3) TO TEST MALE FERTILITY

This application claims benefit of Provisional Application Ser. No. 60/075,079 filed Feb. 19, 1998.

FIELD OF THE INVENTION

This invention relates to male infertility testing, and to uses of recombinant human zona pellucida protein in clinical research and practical applications.

DESCRIPTION OF RELATED ART

Fertilization is the process whereby individual gametes from the female (egg) and male (sperm) unite to create a zygote whose genetic makeup is different from both parents. The sperm-egg interaction requires zona pellucida protein 3 (ZP3) both as a sperm-oocyte binding ligand and as an acrosome reaction inducer.

In male patients with infertility of unknown etiology, an abnormal sperm-zona pellucida interaction between sperm and egg is observed frequently. This abnormality is associated with reduced sperm fertility capacity and may account for a significant proportion of infertility cases. Male infertility is a significant problem today, and approximately 30–40% of infertility cases can be attributed to male reproductive dysfunction. Therefore, there is a fundamental need to gain a deeper understanding of human sperm-oocyte interaction at the zona pellucida level. Greater understanding of this problem will offer improved and more physiopathologically directed therapy to these patients.

Infertility in many cases arises from a problem with binding of egg with sperm to form a zygote. The binding of sperm to the zona pellucida of the egg is a crucial recognition event in this process that leads to fertilization. Extensive investigation of murine fertility systems has resulted in the identification and isolation of zona pellucida protein 3 ("ZP3") as the primary receptor for sperm within the zona pellucida Bleil and Wassarman, *Dev. Biol.* 76: 185–202 (1980). ZP3 is a glycopolypeptide which plays a crucial role during fertilization. As part of its biological role, ZP3 binds to a spermatozoon and produces the acrosome reaction after less than 30 minutes of exposure to the spermatozoon. This biological activity consists of two parts. The first part is binding of ZP3 to a spermatozoon. The second part is induction of the acrosome reaction within a spermatozoon. The two parts can be detected by a number of procedures that are known to the skilled artisan.

Current evidence indicates that, as demonstrated in the murine model, ZP3 is involved in two events necessary for fertilization. First, ZP3 serves as the primary receptor for binding of sperm to the zona pellucida, Saling, *Oxf. Rev. Reprod. Biol.* 11: 339–388 (1989). Second, ZP3 is necessary for induction of the acrosomal reaction, Saling, *Biol. Rep.* 44: 246–251 (1991). Most studies in this area have used native ZP3 obtained from other animals. Reports on the human ZP3 glycopolypeptide indicate that this protein has a molecular weight of about 60 to 100 kD, with about half of this total as carbohydrate.

The biological role of ZP3 carbohydrate in fertility has been surmised but no definite conclusions pertaining to inter species discrimination have been made. In one recent experiment, mouse embroyonal carcinoma cells were transfected with mZP3 in which five serine residues clustered in exon 7, Ser-329, Ser-331, Ser-332, Ser-333 and Ser-334 were converted to small non-hydroxy amino acids by site directed mutagenesis. The transgenic ZP3 was synthesized and secreted in an inactive form, having lost its ability to bind sperm, as described by Chen et al., Proc. Natl. Acad. Sci. USA 95: 6193–97 (1998). However, this work did not adequately address possible interspecies differences between ZP3s and did not adequately characterize differences between the five different serines. Moreover, the specificities of the UDP-GalNAc:polypeptide N-acetylgalactosaminyltransferase family which links the carbohydrate GalNAc to the side chain of certain serine and threonine residues in mucin type glycopolypeptides presently is unknown. However, empirical data already obtained with known mammalian peptide sequences can be used to predict the probability of glycosylation for a given sequence with high confidence, as reported by the Denmark Center for Biological Sequence Analysis. See for example, the center's website at www.cbs.dtu.dk/services/NetOGlyc-2.0, (hereinafter "NetOglyc website"). A database of O-glycosylated proteins can be found in Hansen et al., *Nucl. Acids Res.*, 25: 278–282 (1997) and an algorithm for predicting glycosylation sites based on sequence context is found in Hansen et al., *Glyco. J.*, 15: 115–130 (1998).

Advances in molecular biology have revealed new information about the ZP3 protein and its associated gene(s). Full-length cDNA clones of human ZP3 have been isolated, and the genomic loci of this gene has been characterized as described by Chamberlin and Dean, *Proc. Nat. Acad. Sci. U.S.A.* 87: 6014–6018 (1990). The genomic sequence from mouse has been obtained, and an exon 7 that codes the sequence at the carboxyl terminal end of the protein can be obtained by known methods. Kinloch et al., *Proc. Natl. Acad. Sci. USA* 85: 6409–13 (1988). Clones that contain sequence information from the mouse ZP3 gene express usable quantities of recombinant ZP3 ("rZP3") from, for example, the mouse, in tissue culture lines. Unfortunately, however, the production of recombinant human ZP3 ("rhZP3") is fraught with technical difficulties, not the least is the fact that expression of rhZP3 often leads to a generally unstable protein. Chapman and Barratt, *Mole. Human Repro.* 3:646, 648 (1997). Moreover, properly glycosylated hZP3 has never been purified before, so any information about this material is determined indirectly.

The apparent molecular weight of ZP3 can differ slightly depending on where it was made. For example, Beebe et al., *Dev. Biol.* 151: 48–54 (1992), determined that recombinant murine ZP3 ("rmZP3") derived from transfected chinese hamster ovary ("CHO") cells was about 60 to 70 kDa, which differed in molecular weight from the average size of native ZP3, which is 83 kDa. These researchers attributed this incongruity to a difference in glycosylation pattern.

Despite the putative difference in glycosylation, rmZP3 demonstrated biological activity in homologous (mouse) spermzona pellucida competition assays, and rmZP3 was capable of triggering acrosomal exocytosis in capacitated mouse serum as described by Beebe et al. *Dev. Biol.* 151: 48–54 (1992). When tested in a human system, however, rmZP3 displayed only a partial competitive effect under hemizona assay conditions, and did not function as an acrosome reaction agonist. Chamberlin and Dean, *Proc. Natl. Acad. Sci. USA* 87: 6014–18 (1990).

Another subsequent publication indicated the possible production of rhZP3 from CHO cells having biological activity. Van Duin et al., *Biol. Repro.* 51: 607–17 (1994). However, the authors of the Van Duin report did not demonstrate that rhZP3 made has the capacity to bind sperm. Furthermore, the rhZP3 required at least three hours of contact with spermatozoa at an extremely high 10–20 µg/ml rhZP3 concentration before any significant acrosomal reaction could be seen, the ZP3 cannot be said to possess real biological activity. This conclusion follows from the facts that biological activity is a specific (i.e. can occur at low concentration) binding of spermatozoa to ZP3 protein and also a quick acrosome reaction occurs. The specific binding and quick reaction are a necessary prelude to spermatocyte entry through the zona pellucida. The concentration of ZP3 under more natural biological conditions is at least 100 fold lower that reported by Van Duin, and the biological acrosomal reaction occurs in less than 30 minutes, not a minimum of a few hours.

One means of testing the biological reaction is with hemizona assay (HZA). HZA functionally tests for the assessment of tight binding of sperm to the zona pellucida, a critical step that triggers the physiological acrosome reaction leading to fertilization and early embryo development.

Because of the difficulties in obtaining suitable rhZP3 that could be used in such tests, most work has been carried out with genes from other species. Despite the problems it is now known that human ZP3, like mouse ZP3, comprises approximately 50% carbohydrate, (i.e. between 40% to 60% carbohydrate by weight) and the 424 amino acid long polypeptide differs from the mouse sequence by about one third. Also, it is generally understood that different host cell types may glycosylate hZP3 differently. However, "Whether such differences would alter the biological activity of rhZP3 is equivocal" as summarized recently. (Id. at p. 648).

Large quantities of biologically active hZP3 are needed for clinical applications that exploit the critical event of sperm binding to the zona pellucida, to diagnose a clinical condition. For example, a standardized and internally controlled "hemizona assay" tests this event in evaluating the binding capacity of human spermatozoa to human zona pellucida as described by Burkman et al., *Fertil. Steril.* 49: 688–693 (1988) and Oehninger et al., *Andrologia* 24: 307–321 (1992). Unfortunately, this need cannot be met from animal sources, or from presently available rhZP3. Thus, a procedure is desired to obtain large quantities of reproducible quality material with one or more biological properties of hZP3 both for research use and for diagnostic tests and pharmaceuticals that require a fully active protein.

SUMMARY OF THE INVENTION

It is an object of the present invention to provide glycopolypeptide having one or more biological properties of hZP3. It is another object to provide isolated and biologically functional rhZP3 protein. It is yet another object to provide rhZP3 glycopolypeptide that binds human sperm and that has diagnostic and therapeutic use related to human fertility. Yet another purpose is to provide methods for testing male infertility, based on induction of the acrosome reaction caused by binding of biologically active hZP3 to clinical sample materials. Yet another purpose is to provide high levels of biologically active hZP3 of consistent quality for use in the clinical and research chemistry.

In achieving these objectives and other objects, the invention provides a recombinant glycopolypeptide of about 65 kd to about 100 kd that comprises approximately 50% carbohydrate in terms of weight and that can bind human spermatozoa and induce an acrosome reaction. The invention also provides a recombinant glycopolypeptide of about 65 kd to about 100 kd that comprises approximately 50% carbohydrate by weight and that can bind human spermatozoa and induce an acrosome reaction, wherein the glycopolypeptide pattern is produced by a cell having glycosylation machinery similar to that of an oocyte. The invention further provides a process for producing a glycopolypeptide having the biological activity of hZP3 protein, comprising the steps of: transfecting an ovarian cell line cell with a gene that encodes a hZP3 polypeptide; culturing the cell to produce a culture of hZP3 producing cells; and isolating the glycopolypeptide.

The invention also includes a method of detecting male infertility from a semen sample, comprising the steps of: contacting a solution of recombinant glycopolypeptide of about 65 kd to about 100 kd that comprises approximately 50% carbohydrate by weight and that can bind to human spermatozoa and induce an acrosome reaction with spermatozoa from the sample to form an admixture; detecting the acrosome reaction and acrosomal lysis in the admixture; and comparing the amount of acrosomal lysis with a reference value. The invention further provides a cell from a transformed human ovarian cell line comprising a rhZP3 gene.

Another embodiment of the invention is a transgenic glycopolypeptide having an active portion (i.e. glycosylated amino acid sequence region) that preferentially binds to human sperm, wherein the active portion has a polypeptide size of less than 25 kDa, comprises an amino acid sequence that is more than 54% identical with SEQ ID NO: 2 and exhibits a predicted O-glycosylation site at the fifth position from the carboxyl terminus. Yet another embodiment is a method of detecting male infertility from a spermatozoa sample, comprising the steps of: (a) contacting transgenic glycopolypeptide having an active portion that preferentially binds to human sperm, wherein the active portion has a polypeptide size of less than 25 kDa, comprises an amino acid sequence that is more than 54% homologous with SEQ ID NO: 2 and exhibits a predicted O-glycosylation site at the fifth position from the carboxyl terminus, with spermatozoa from said sample to form an admixture; (b) detecting biological activity of said spermatozoa in said admixture; and (c) comparing the biological activity with a reference value. Yet another embodiment is a nucleic acid vector useful for producing a glycopolypeptide, the glycopolypeptide specifically binds to human sperm, wherein the vector codes for an amino acid sequence that is more than 54% homologous with SEQ ID NO: 2. Yet another embodiment is a human cell containing a nucleic acid vector useful for producing a glycopolypeptide less than 200 amino acids long, wherein the glycopolypeptide specifically binds to human sperm and the vector codes for an amino acid sequence that is more than 75% identical with SEQ ID NO: 2.

DESCRIPTION OF THE FIGURES

FIG. 1 is the amino acid sequence (SEQ ID NO: 2) for residues 308 to 348 of human ZP3.

FIG. 2 is a representative prediction summary of O-glycosylation sites on the 308–348 amino acid region (SEQ ID NO: 2) of human ZP3.

FIG. 3 is a representative prediction summary of O-glycosylation sites on the 309–349 amino acid region (SEQ ID NO: 3) of mouse ZP3.

DETAILED DESCRIPTION OF THE PREFERRED EMBODIMENTS

The inventors have discovered that tissue-specific and species-specific differences in glycosylation pattern of the hZP3 protein, and more particularly the role of residues 308 through 348, greatly affect the biological activity of this protein. From this discovery, the inventors have developed a cell expression system that uses the ovarian glycosylation machinery to properly glycosylate hZP3. The inventors also have developed glycopolypeptides that bind human sperm. "Properly glycosylate," in this context means to give a glycosylation pattern that is similar to that of the human oocyte (is "human-functional") such that the glycopolypeptide has biological activity (i.e. specific binding to oocyte) with human sperm. Using the present system, the inventors have isolated rhZP3 for the first time that, unlike previous rhZP3, is fully biologically active and contains carbohydrate that more closely resembles human oocyte protein compared to previously known rhZP3. The inventors also have developed a test using the biologically active recombinant glycopolypeptide to diagnose causes of male infertility. Furthermore, the inventors have discovered therapeutic uses of rhZP3 and rhZP3 glycopolypeptides smaller than rhZP3 that have not been realized before.

Based on their understanding of the role of hZP3 residues 308 through 348 in specifying human oocyte glycosylation, the inventors have discovered alternative biologically functional glycopolypeptides that simulate binding of human oocyte to human sperm. The term "biologically functional glycopolypeptide" in this context means a polypeptide that comprises at least the segment of amino acids having the sequence SEQ ID NO: 2 and which binds to human sperm better than to mouse sperm. Preferably the polypeptide further comprises carbohydrate that has been added by a human cell during polypeptide synthesis. More preferably the human cell is from an ovary or follicle cell line. In one embodiment the cell line is a non-ovarian mammalian (and preferably human) cell line that has been genetically altered for the induction and/or simulation of oocyte glycosylation enzymes. In this context, large scale production of small glycopolypeptides of less than 200 amino acids having sequence identity of more than 54% and preferably more than 75% with SEQ ID NO: 2 allows new uses such as, for example, contraception, whereby the glycopolypeptide interferes with normal fertilization.

The inventors discovered that the biological specificity of rhZP3 predominantly comes from the carbohydrate portion of this section of hZP3. More specifically, the inventors have discovered that human rZP3 made by non-human ovarian cell lines such as a CHO cell line, while having the same amino acid sequence as human ZP3, are not active with human eggs because of their carbohydrate component. For example, removal of carbohydrate from hZP3 by a glycosidase will remove the biological activity of the hZP3. The precise differences in glycosylation can be determined by first making a hZP3 having full biological activity. Then, the carbohydrate portion of the glycopolypeptide can be partly altered or removed. After alteration, the glycopolypeptide is tested to see if it retains full activity with human eggs.

The inventors' knowledge of the subtle biochemical differences between human and mouse ZP3 that directly account for the interspecies discrimination of this protein, provides new tools and techniques for both creating and using glycosylated glycopolypeptide for diagnoses and therapies related to human fertility. More specifically, the primary sequence of ZP3, contrary to many held beliefs, directs a different glycosylation, which, together with the related and unique species-specific and tissue-specific glycosylation machinery in the human oocyte, provides a unique human oocyte glycosylation pattern. Thus, one aspect of the invention is the discovery that human specific oocyte glycosyation in human oocytes does indeed matter when expressing the ZP3 protein. Another aspect of the invention is that the amino acid sequence within residues 308 to 348 of ZP3 effects and directs human specific oocyte glycosylation, being species specific. Yet another aspect of the invention is that changes to this specific sequence can be made according to predictive features of an algorithm specifically designed to look for the effect of sequence on the probability of O-glycosylation within that sequence.

The discovery of a species-specific binding region within hZP3 provides the ability to improve potency of glycopolypeptides that mimic the one or more biological activities of hZP3. Thus, another aspect of the invention is that a smaller glycopolypeptide, comprising less than 400 amino acids can be expressed having the binding ability of human ZP3 by virtue of the presence of an active region that is glycosylated in a human-functional pattern (i.e. with human-like carbohydrate suitable for species specific function with human spermatozoa). Specific human-like carbohydrate useful in this context is characterized and explained by, for example, Clark, et al., Human Reproduction 11: 467–473 (1996); Clark et al., Molecular Human Reproduction 2: 513–517 (1996); Patankar et al., Molecular Human Reproduction 3: 501–505 (1997); and Ozgur et al., Molecular Human Reproduction 4(4): 318–324 (1998).

In advantageous embodiments the glycopolypeptide is between 41 to 400 amino acids long. When used primarily for the species-specific binding reaction, the glycopolypeptide should be smaller, such as between 41 to 300, 50 to 200, 50 to 150 and even 50 to 100 amino acids long to allow greater binding sites for a given amount of material. Most advantageous for binding reactions is a glycopolypeptide that shares at least 54% sequence identity, particularly greater than 75% sequence identity, and most particularly greater than 80% sequence identity with SEQ ID NO: 2 and that is between 41 and 65 amino acids long.

The glycosylation advantageously is carried out by expression in human cells (i.e. cells that express human glycosylation enzymes) and particularly is carried out by expression in a human follicle cell line or ovarian cell line such as PA-1. In other embodiments, the glycopolypeptide that contains this region, shown in SEQ ID NO: 2, can be as small as 41 amino acids long. However, advantageously, a large glycopolypeptide up to 200, 400 or even more amino acids long or may be made from repeated units of the binding portion shown in SEQ ID NO: 2.

In the context of using the species-specific region, the inventors discovered 3 parameters. One, residues 308 to 348 of ZP3 contain interspecies information and nucleic acid vectors that contain the human residues 308 to 348 of ZP3 are particularly useful to make polypeptides having human-specific glycosylation. Two, the amino acids encoded by residues 308 to 348 as shown in SEQ ID NO: 2, differ from that of ZP3 found in other species, particularly in the capability of serines to become O-glycosylated by cellular machinery. Three, in contrast to N-glycosylation, the pattern of predicted O-glycosylation of the residues 308 to 348 carboxyl terminal serines in peptides or peptides comprising the sequence greatly affects the actual glycosylation of a polypeptide.

The inventors discovered that the human ZP3 sequence has a serine 344 residue which is most likely glycosylated. In contrast, a corresponding sequence from another species such as, for example, the mouse, shows a greatly different predicted O-glycosylation probability. For example, the analagous residue (345 serine) in mouse has drastically less predicted glycosylation, and instead, the 332 serine stands out as being most likely glycosylated. Thus, the discovered technique can be used to distinguish and to predict which sequences and sequence modifications can provide a suitable human sequence that will become glycosylated in human cells, and in particularly cells from a human ovary or follicle cell line. FIGS. 2 and 3 depict the respective predictive O-glycosylation parameters. As seen in these figures, the higher the potential value with respect to its corresponding threshold value, the greater chance that the amino acid will react with an N-acetylgalactosaminyltransferase. More specifically, the "potential" value is a relative measure of whether the designated residue should be O-glycosylated. The "threshold" value is a relative measure that inversely relates to the chances of glycosylation.

The inventors point out that the output shown in FIGS. 2 and 3 reflects empirical knowledge obtained from proteins found in other, non-ovarian cells and is a relative measure. Clearly this analysis shows that, based on the influence of sequence on glycosylation in other systems, the glycosylation of residues 308 to 348 of human ZP3 is primarily directed to position 344, whereas the corresponding mouse sequence has glycosylation directed to 13 positions to the amino terminal side of that serine residue. Furthermore, altering the human sequence in a manner to remove this calculated propensity for O-glycosylation will also decrease the affinity of the glycosylated polypeptide for the human sperm surface. The analysis used here can be used to derive other sequences contemplated as the invention. In particular, amino acid substitutions can be made to residues at positions listed in Table 1, which preserve the unique human-species specific glycosylation of the glycopolypeptide of the invention. This table lists representative amino acids that, according to the algorithm can be substituted while maintaining the unique human glycosylation pattern.

For most positions, exemplified by position 326, a conservative amino acid substitution can be made. By "conservative" substitutions is meant replacing an amino acid residue with another that is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Preferably, the portion of the sequence that is intended to mimic substantially the peptide of SEQ ID NO: 2 will differ less than 50% from SEQ ID NO:2, except where additional amino acids may be added at either terminus.

A considerable amount of work in this area has provided algorithms to use in making such changes. For example, the hydropathic index of amino acids may be considered. The importance of the hydropathic amino acid index in conferring interactive biologic function on a protein is generally understood in the art as cited in U.S. Pat. No. 5,703,057. It is accepted that the relative hydropathic character of the amino acid contributes to the secondary structure of the resultant peptide which in turn defines the interaction of the peptide with other molecules, for example, receptors, DNA, glycosidases, and the like. Each amino acid has been assigned a hydropathic index on the basis of its hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3 .5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent peptide. In making such changes, the substitution of amino acids whose hydropathic indices are within +−2 is preferred, those which are within +−1 are particularly preferred, and those within +−0.5 are even more particularly preferred. It is also understood in the art that the substitution of like amino acids can be made effectively on the basis of hydrophilicity. U.S. Pat. No. 4,554,101, for example, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0+−1); glutamate (+3.0+−1); serine (+0.3); asparagine (+0.2); glutamine (+0.2); glycine (0); threonine (−0.4); proline (−0.5+−1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent peptide. In such changes, the substitution of amino acids whose hydrophilicity values are within +−2 is preferred, those which are within +−1 are particularly preferred, and those within +−0.5 are even more particularly preferred. As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. In the present case, the inventors discovered that, with the exception of substitutions shown in Table 1, serines in SEQ ID NO: 2 cannot be substituted because of their role in glycosylation.

A "biologically functional" glycopolypeptide or rhZP3, in the context of the present invention means that the polypeptide (containing as a minimum amino acids 308 to 348, and functional derivatives thereof) or the ZP3 (if the whole protein is made) binds spermatozoa when present at a concentration below 1 μg/ml, and induces an acrosome reaction within about one hour upon binding. Advantageously, the rhZP3 binds when present at a concentration below 0.1 μg/ml and most advantageously when present at a concentration of 0.01 μg/ml to 0.1 μg/ml. The time of the acrosome reaction can be less than 1 hour or even less than 30 minutes. This binding of ZP3 protein to spermatozoa is species specific and also can be used to detect deficiencies in spermatozoa that account for male infertility.

An "ovarian cell line" as termed here means a human cell line from an ovary tissue such that cells of this line produce glycopolypeptide having characteristic carbohydrate of oocyte glycopolypeptides. An oocyte-like glycopolypeptide carbohydrate pattern can be compared with a non-oocyte-like glycopolypeptide pattern by any of a number of techniques well-known to a skilled artisan.

Methods for comparing glycopolypeptide patterns in the context used above include, for example, the use of monoclonal antibodies, as described by Barbosa to detect changes in the carbohydrate portion of HLA glycopolypeptide, using oligonucleotide-directed mutagenesis, gene transfer techniques (Barbosa et al., *J. Exp. Med.* 166: 1329–50 (1987)) and newer biochemical methods to directly assess carbohydrate content.

Another method that can be used to directly compare whether a recombinant glycopolypeptide has a correct glycosylation pattern is to determine whether the glycopolypeptide can block sperm binding to native oocytes in a "hemizona assay." In normal conditions without the glycopolypeptide, the sperm binds to oocytes. However, when glycopolypeptide having proper oocyte glycosylation is incubated with the sperm, the glycopolypeptide will bind to the sperm first and block the sperm from further binding or reacting with the oocyte. In contrast, if the glycopolypeptide lacks a correct glycosylation pattern, the glycopolypeptide will not block sperm binding to the oocyte.

Yet another method of determining whether a glycopolypeptide possesses a correct glycosylation pattern is to remove carbohydrate side chains from the glycopolypeptide with peptide N-glycosylase F and O-glyconase and then incubate reaction products with sperm. If the glycopolypeptide preparation can block sperm binding to a human oocyte before digestion but cannot after digestion, then the undigested preparation possesses a correct glycosylation pattern.

A "recombinant human zona pellucida protein 3" means a transgenic protein (or native protein under the control of a transgenic control element) that comprises at least part of the hZP3 gene and which retains substantially all of the hZP3 glycopolypeptide activity. "Substantially all" means that the protein exhibits binding activity and stimulation of the acrosome reaction when co-present with spermatozoa in aqueous solution at a concentration of less than about 1 µg/ml (e.g. 1 µg/ml), and particularly less than about 0.1 µg/ml (e.g. 0.1 µg/ml), for a time period of less than about 1 hour (e.g. 1 hour), and particularly, less than about 30 minutes (e.g. 30 minutes).

DNA sequences useful for complete hZP3 transgenic protein expression are known by the skilled artisan and derived from the known 424 amino acid sequence of hZP3, which is described by Chamberlin and Dean, *Proc. Nat. Acad. Sci. U.S.A.* 87: 6014–6018 (1990). The transduction of cells from an ovarian cell line with such a sequence can be effected via known methods. Generally, a DNA construct is used that contains a promoter upstream of the structural gene that encodes the desired protein sequence. Suitable promoters are described, for example, in U.S. Pat. No. 5,618,698. According to this embodiment, both a rhZP3 structural gene and a regulatory element to control the gene are transduced into the host cell.

According to another embodiment of the invention, a cell from an ovarian cell line is transduced ex vivo with a DNA comprising a promoter and a homologous DNA (but not an intact structural gene) that can link up with and function (i.e., turn on or increase expression) with an endogenous gene within the nucleus of the cell. In this embodiment, DNA comprising a regulatory sequence, an exon and a splice donor are introduced into a cell by homologous recombination into the cell's genome at a preselected site. The introduction of this DNA results in the production of a new transcription unit in which the regulatory sequence, exon and splice donor site are operatively linked to the endogenous gene.

The phrase "operably linked" refers to a first sequence(s) being positioned sufficiently proximal to a second sequence(s) so that the first sequence(s) can exert influence over the second sequence(s) or a region under control of that second sequence. For instance, a regulatory sequence can be operably linked to a promoter, whereby this sequence enhances the transcriptional strength of the promoter. In this situation, the regulatory sequence would typically be 5' to the promoter. The regulatory sequence and promoter can, in turn, be operably linked to a gene so that the gene will be expressed under the control of the regulatory sequence/promoter combination, which would typically be 5' to the gene.

The introduction of DNA typically is followed by selection of cells that have received a promoter in a desired location to turn on the desired gene. Applicable selection methodology is described, for instance, in U.S. Pat. Nos. 5,641,670 and 5,272,071. Selection techniques also are described by Mansour et al., *Nature* 136: 348, 349 (1988). After selection, the cells which express the desired gene are cultured and the expressed gene product is harvested.

According to preferred embodiments the DNA sequence useful for hZP3 transgenic expression codes for a shorter protein (polypeptide) molecule, (i.e. less than 25 kDa polypeptide, particularly less than 10 kDa polypeptide and more particularly less than 5 kDa). Such preferred protein sequences include a core region as shown in SEQ ID NO: 2. The inventors realized that SEQ ID NO: 2 is the most important determinant with respect to the inter-species glycosylation pattern of ZP3 and that a small protein having this sequence, for a given mass, will be particularly potent in binding sperm. The SEQ ID NO: 2 is 54% homologous with the corresponding sequence from mouse ZP3. By "homologous" is meant that when the two sequences are compared, 54% of the amino acids are the same. Despite the homology, the mouse ZP3 has a small amount of binding with human sperm, although this affinity is less than one-tenth, and typically less than one-hundredth the level observed with human ZP3. The term "can strongly bind human spermatozoa" is used herein to mean binding that is at least about 10 times (e.g. 10 times) as strong as an equivalent molar amount of mouse ZP3. In practice, such a qualitative determination is carried out by incubating different concentrations of material in a binding assay and determining binding directly or indirectly by competition. Such binding assays are exemplified in the examples herein and are well known to the skilled artisan. Thus, a peptide sequence that differs from human ZP3 by up to 46% maintains some residual human sperm binding activity that is stronger than the equivalent molar amount of mouse ZP3. Accordingly, a peptide according to one embodiment is more than 46% identical to the human ZP3 sequence shown in SEQ ID NO: 2. Furthermore, it is preferred that any deviation from this sequence be limited to positions 3, 8, 13, 16, 17, 19, 21–23, 25, 27, 28, 30, 32–35, 38 and 39, (positions listed in Table 1) as the non-listed positions are more conserved.

In another embodiment the sequence is identical with the last 11 amino acids at the carboxyl terminal end of the portion depicted in FIG. 1. This is because the serine in the middle of this sequence is particularly important for the human specific glycosylation.

In yet another embodiment the invention is a nucleic acid reagent vector that comprises a DNA sequence that codes for SEQ ID NO: 2. Such vector advantageously is a carrier for delivery of a gene sequence for expression of the ZP3 binding activity. In one embodiment the vector comprises residues 308 to 348 but lacks the remainder of the ZP3 coding gene. Construction of such a carrier is known to the skilled artisan as described, for example in the references cited herein. According to this last embodiment a glycosylated polypeptide useful for diagnostics and pharmaceutics related to effects on binding sperm and human fertility, is contemplated that is made by a vector comprising the human residues 308 to 348 or other DNA that codes for SEQ ID NO: 2.

The term "rhZP3 analog" refers to hZP3 mutants and chemically altered derivatives that have the above-listed biochemical and biological attributes of native rhZP3. In particular, changes in the amino acid sequence of hZP3 are contemplated in the present invention. hZP3 can be altered by changing the DNA encoding the protein. Preferably, only conservative amino acid alterations are undertaken, using amino acids that have the same or similar properties and the glycosylation recognition sites are not altered as described above.

Additionally, other variants and derivatized species of hZP3 can be used in the present invention. Variants include analogs, homologs, derivatives, muteins and mimetics of hZP3 that retain the ability to bind spermatozoa and induce the acrosome reaction. Fragments of the hZP3 refer to portions of the amino acid sequence of hZP3 that also retain this ability. The variants and fragments can be generated directly from hZP3 itself by chemical modification, by proteolytic enzyme digestion, or by combinations thereof. Additionally, genetic engineering of non-ovarian cell lines to alter their protein glycosylation machinery to emulate that of the oocyte could be carried out to allow expression of hZP3 protein in non-oocyte cells.

Variants and fragments (i.e. analogs) of rhZP3 also can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. Eds., J. Wiley & Sons 1989 & Supp. 1990–93); PROTEIN ENGINEERING (Oxender & Fox Eds., A. Liss, Inc. 1987). In addition, linker-scanning and PCR-mediated techniques can be employed for mutagenesis. See PCR TECHNOLOGY (Erlich Ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra. One preferred variant in this context is a hrZP3 424 amino acid sequence having six histidine amino acids added to the amino terminal end. The added portion allows more convenient affinity purification of the synthesized protein with Ni-NTA affinity resin.

Recombinant hZP3 protein made by cultured cells according to the present invention can be purified by a number of techniques known to the skilled artisan. A preferred method is to collect cell culture media from cells that make the rhZP3 protein and then purify this protein by affinity chromatography. A lectin column, particularly a wheat germ agglutinin column, is preferred for affinity chromatography. Also preferred is to use Ni-NTA affinity resin and to elute protein from this resin at a low pH, in combination with a rhZP3 analog such as that mentioned above having a polyhistidine portion.

The present disclosure permits large-scale expression of biologically active hZP3 glycopolypeptide by recombinant DNA methods. The glycopolypeptide thereby can be obtained in an isolated form by known recombinant methods. The term "isolated" in the context of proteins denotes a degree of purification such that the hZP3 is free of other human proteins that are found with hZP3 in its native context. The isolated protein preferably would be in homogeneous form, that is, in a form amenable to protein sequencing on a gas-phase sequenator, which are available from manufactures such as Applied Biosystems, Inc. Techniques for obtaining such homogeneity after recombinant production include SDS-PAGE, isoelectric focusing, chromatographic electrophoresis, ion exchange chromatography, gel exclusion chromatography, affinity chromatography, immunoprecipitation, and combinations thereof.

Purify denotes a degree of separation that is higher than isolation. A "purified" protein is sufficiently free of other materials such that the any impurities do not unduly affect the biological properties of the protein or cause other adverse consequences.

The pure or partially purified protein of the invention can be used for many research and clinical purposes. One preferred use is for fertility testing. In this case, rhZP3 is combined with a sample of spermatozoa. Recombinant hZP3 then binds to spermatozoa to produce an acrosome reaction and the reaction is detected. A detectable difference in the proportion of spermatozoa that react indicates male fertility or infertility. Spermatozoa from a fertile male will successfully undergo acrosome reactions at a higher rate than spermatozoa from an infertile male.

In a preferred procedure, semen from a patient donor and control semen from a donor known to have properly functioning sperm, are allowed to liquefy at room temperature. Motile spermatozoa within each liquid sample are selected by mixing the liquid with buffered protein solution followed by centrifugation, an incubation period of a few minutes to allow spermatozoa to swim up, and removal of an upper fluid portion. Active sperm preferably are exposed to 1–100 ng/ml rhZP3 and more preferably to 5–10 ng/ml rhZP3 for at least 5 minutes. After this time, the acrosomal status is determined by comparing control sperm with the patient test sperm by any of a number of techniques known to the skilled artisan.

Both binding and acrosome reaction can be tested for detecting rhZP3 biological activity. For binding tests, rhZP3 is used in detecting the initial stage of binding sperm to zona pellucida. In other embodiments, the recognition and binding of a sperm sample to rhZP3 is directly tested in solution, or after immobilization of rhZP3 to a solid support such as SEPHADEX (hydroxypropylated, cross-linked dextran matrix or beads) or an agarose resin. These functional tests evaluate the binding capacity of sperm, and can use (a) rhZP3 conjugated beads (solid phase) or, (b) as part of an ELISA-like test, rhZP3 free in solution (liquid phase). In the latter case, rhZP3 preferably is conjugated to another moiety that can form a signal in the assay. Sperm from infertile male individuals, and that lack ZP3 binding activity will not bind to rhZP3 and hence, can be diagnosed and identified.

Acrosome reaction tests typically link one of the male infertility factors with the inability of sperm to undergo the acrosome reaction, an important phase that contributes to the penetration of sperm into the egg. A preferred embodiment in this context is the differential staining and visual counting of total cells and acrosome depleted cells after treatment with hrZP3. The etiology of a patient can be determined if the patient's sperm responds to treatment with rhZP3. This response can be detected, for example, by immunofluorescence techniques that are known to the skilled artisan.

In another embodiment, the present invention relates to transformed, human ovarian cell lines, the cells of which contain DNA encoding transfected ZP3. Suitable cell types include but are not limited to, cells of the following types: $EB_2$, (human ovary cells, ATCC), CaoV-3, CaoV-4, OVCAR-3, SK-OV-3, SW 626 (human ovary, carcinoma, ATCC). Such cells are described, for example, in the Cell Line Catalog of the American Type Culture Collection (ATCC). The transfer of genes into mammalian cells, to produce a "transfected" cell line, has been well described in the art. See, for example, Ausubel et al., *Introduction of DNA Into Mammalian Cells*, in CURRENT PROTOCOLS IN MOLECULAR BIOLOGY, sections 9.5.1–9.5.6 (John Wiley & Sons, Inc. 1995).

In yet another embodiment, the invention provides therapeutic uses of rhZP3 as a "priming sperm stimulant" in intrauterine insemination therapy ("IUI"). In this procedure, a swim-up procedure is employed to prepare sperm. The inventors have discovered that incubating these sperm with rhZP3 before this swim-up procedure will stimulate an acrosome reaction in some of the sperm and thereby exerts a priming effect on the sperm sample. This priming effect allows the treated sperm to respond more efficiently to motility and acrosome reaction regulators within the female reproductive tract.

In this therapeutic embodiment, sperm are incubated with a rhZP3 dose previously shown to produce a moderate stimulation of the acrosome reaction. Moderate stimulation in this context means that the reaction is stimulated in approximately 10–15 percent of the sperm within a given sample. The incubation step preferably is for at least 30 minutes and is followed by a washing step and the swim-up procedure.

In another therapeutic application, rhZP3 is used to stimulate the acrosome reaction prior to intracytoplasmic sperm injection (ICSI) therapy. Use of rhZP3 in this case can benefit fertilization by, for example, increasing the rate of successful fertilization. Preferably, rhZP3 is added to a suspension of sperm and then washed from this suspension prior to bringing a spermatozoan into an oocyte. In this case, the rhZP3 is used in a high concentration to ensure that a maximum proportion of treated sperm experience an acrosome reaction.

The present invention is further described by reference to the following, illustrative examples, which do not limit the scope of the claimed invention.

EXAMPLE 1

Reverse Transcriptase Polymerase Chain Reaction of hZP3 cDNA

A pair of primers (A and B primers) was designed from the reported sequence of hZP3. Chamberlin and Dean supra. Primer A is located at the 5' end of the hZP3 cDNA from bases 8 to 29 as 5'ACCATGGAGCTGAGCTATAGG3'(SEQ ID NO: 4). Primer B is located at the 3' end of the hZP3 cDNA from bases 1256 to 1282 as 5'TTCTCGAGTTAATGATGATGATGATGATGATCGGAAGCAGACACAGGGTGGG AGGCAGT3'(SEQ ID NO: 5). A sequence at an XhoI restriction Site (CTCGAG) and a sequence coding for 6 histidine residues were added to the 3' end of primer B for the purpose of subcloning the cDNA into the expression vector as well as for purification of the hZP3 from the medium.

A total RNA extract was isolated from human ovary tissue. RT-PCR was performed and RT-PCR was used as the "standard method" described by Perkin-Elmer Cetus (Foster City, Calif.). A 1315 base pair DNA fragment comprising the full length of hZP3 cDNA with a 6 histidine tail and an XhoI restriction site was obtained by PCR amplification of the first strand cDNA from the ovary mRNA.

EXAMPLE 2

Subcloning hZP3 cDNA into pcDNA 3.1(+) Expression Vector

The RT-PCR product from Example 1 was separated by agarose gel electrophoresis and purified with a Geneclean II kit (BLO 101, Vista, Calif.) after cutting out the 1315 bp DNA product. The purified RT-PCT DNA fragment was inserted into a mammalian Expression Vector, pcDNA 3.1 (+) (Invitrogen, San Diego, Calif.) which can express high levels of recombinant protein in mammalian cells and also contains a neomycin resistant gene for selection. The pcDNA 3.1(+) vector with hZP3 cDNA was transformed into *E. Coli* cells. The positive clones were identified by restriction mapping, southern blot analysis and DNA sequencing.

DNA sequence analysis of hZP3 cDNA revealed that the hZP3 cDNA sequence is identical to that published by Chamberlin and Dean, *Proc. Nat. Acad. Sci. U.S.A.* 87: 6014–6018 (1990). To determine whether the hZP3 cDNA could be translated into a full length recombinant hZP3, in vitro translation was carried out (Promega, Madison, Wis.). SDS PAGE Analysis of products from the in vitro translation revealed that hZP3 cDNA produced only a 47 kd protein. This 47 kd was determined to represent the full length form of recombinant hZP3.

EXAMPLE 3

Stable Introduction of rhZP3 into PA-1 Cells

The hZP3/pcDNA3.1(+) construct was introduced into cells of an ovarian cell line "PA-1" by the calcium phosphate method. Selection of cells having a stably integrated exogenous gene was carried out with 200 uM neomycin (Sigma, St. Louis, Mo.). The integration of hZP3 into genomic DNA of the host cell was identified by PCR and southern blotting. In the PCR analysis, integration of the hZP3/pcDNA3.1(+) construct was identified using a specific primer which is located on the pcDNA3.1(+) vector (T7 primer, Invitrogen) with primer B, which is located at the 3' end of hZP3. An expected product was obtained only in stably transfected cells but not in untransfected PA-1 cells, indicating successful integration into the PA-1 cell chromosome.

Expression of recombinant hZP3 was detected by RT-PCR and western blot analysis. RT-PCR analysis of mRNA from stably transfected PA-1 cells and non-transfected PA-1 cells with primer A and B revealed that a PCR amplification product was only observed in the stably transfected cells. Culture medium was harvested from both groups of cells, concentrated by speed vacuum and analyzed by SDS PAGE. The samples were blotted to the nitrocellulose and hybridized to a rabbit polyclonal antibody (Ab5a) which can recognize the conserved region of hZP3. A hybridized signal was only observed from transfected PA-1 cells and the solubilized control protein, indicating rhZP3 expression from the stably transformed cells. Cells were stored in liquid nitrogen.

Experiment 4: Cell Culture of Stably Transfected PA-1 Cells

A stored 1 ml sample of cells was removed from liquid nitrogen and thawed in a 37° water bath for two minutes. The cells were suspended in 5 ml of MEM with 10% FBS and centrifuged at 1000×g for 5 minutes. The cell pellet was resuspended in 10 ml of MEM with 10% FBS and 200 uM neomycin, and then cultured in a 100 mm culture plate. After reaching 90% confluence, cells were removed from the plate using trypsin-EDTA (Sigma, St. Louis, Mo.) and washed with serum free MEM medium. The cell pellet was resuspended in 60 ml of MEM with 10% FBS and 200 uM neomycin and cultured in three 150 mm culture plates. After reaching 50% confluence, the medium was switched from MEM/10% FBS to protein-free hybridoma medium. The medium was collected every 24 hours and proteinase inhibitors (EDTA, leupeptin, pepstatin, PMSF) were added to protect proteins from proteolytic digestion. The collected media were stored at −20° C. until used.

Experiment 5: Purification of Recombinant hZP3 by Affinity Chromatography

The collected medium was thawed at 37° C. and glycopolypeptides were purified by passage through a WGA affinity column (2×4 cm). After applying the medium through the column twice at a flow rate of 3 column volumes per hour, the WGA column was washed with 10 mM PBS, 0.15M NaCl, pH 7.2–7.5 until the 280 nm absorbance of the effluent fell below 0.01. Glycopolypeptides were eluted with 40M phosphate and 0.15M NaCl at pH 3.0–3.1 that contained 0.5M N-acetyl-D-glucosamine.

The partially purified protein from the WGA affinity chromatography was dialyzed with 50 mM Na-phosphate, 10 mM imidazole, and 300 mM NaCl overnight at pH 8.0 at 4° C. and then loaded onto a Ni-NTA column (Qiagen, Valencia, Calif.) at 3–4 column volumes per hour. The column was washed with 50 mM Na-Phosphate, 300 mM NaCl, 10% glycerol at pH 7.8–8.0 until the eluant absorbance at 280 nm fell below 0.01. The hZP3 then was eluted with 200 mM Na-phosphate, 300 mM NaCl at pH 6.6. The eluted protein was dialyzed with 10 mM Na-phosphate pH 7.5 overnight at 4° C. The dialyzed protein was studied by SDS PAGE western blot with an hZP3 antibody. Bands were observed from 65 kd to 100 kd, indicating the presence of hZP3 isoforms.

Experiment 6: Purification of rhZP3 to 80% Purity

Agarose-wheat germ agglutinin (WGA) (Vectoe Laboratories, Inc. Burlingame, Calif.) chromatography was used as a first step to isolate glycoproteins from the cultured cell media. Agarose-wheat germ agglutinin was equilibrated with 10 resin volume of WGA binding buffer (10 mM PBS, pH 7.4, 0.15 M NaCl). The collected supernatants were passed through the WGA resin at a flow rate of 3 resin-volumes per hour in a 4° C. cold room. The resin was washed with WGA binding buffer until the flow-through 280 nm absorbance was less that 0.01. Glycoproteins binding to the WGA resin were separated into two elution peaks with elution buffer A (10 mM PBS, pH 7.4, 0.15 M NaCL, 500 mMN-acetyl-D-glucosamine (Sigma)) and elution buffer B (10 mM PBS, pH 7.4, 0.15 M NaCl, 500 mM N-acetyl-D-glucosamine). After eluting glycoproteins from the resin, the resin was washed with WGA binding buffer until the flow-through 280 nm absorbance was less than 0.01, and then followed by washing with 5 resin volume of WGA storage buffer [10 mM PBS, pH 7.4, 0.15 M NaCl, 20 mM N-acetyl-D-glucosamine, 0.08% sodium azide (Sigma)]. Eluted glycoprotien samples were dialyzed against the Ni-NTA binding buffer (50 mM PBS, pH 8.0; 300 mM NaCl) for Ni-NTA affinity purification.

Histidine tagged glycoprotein (rhZP3) was purified from the glycoprotein fraction, and isolated from cultured cell media with WGA affinity chromatography, with Ni-NTA (nitrilo-tri-acetic acid) resin (Qiagen). Proteins containing one or more 6xHis affinity tags, located at either the amino or carboxyl terminates of the protein, bind to the Ni-NTA resin with an affinity (Kd=10 13 at pH 8.0) far greater than the affinity between most antibodies and antigens, or enzymes substrates suspended 50% slurry of Ni-NTA resin were transferred into the column. Two milliliter of resin were completely resuspended then washed with 5 resin-volume of H20. The resin was equilibrated with 10 resin-volumes of Ni-NTA binding buffer. The WGA isolated glycoprotein samples that had been dialyzed with Ni-NTA binding buffer were passed through an equilibrated Ni-NTA column that contained 1 ml of resin. The flow rate was adjusted to 3–4 resin volumes per hour. After passing the glycoprotein sample through the Ni-NTA column, the resin was washed with 10 resin columns of Ni-NTA binding buffer that contained TWEEN 20 (Fisher)(polyoxyethylene sorbitan monolaurate) and 2-mercaptoethanol, was followed by a wash with Ni-NTA washing buffer (50 mM PBS, pH 6.6, 300 mM NaCL) until the flow-through 280 nm absorbance was less than 0.01. His-tagged glycoproteins were eluted from the resin with the Ni-NTA washing buffer that contained 40 mM of imidazole (Sigma).

The centricon 50 filtration was applied to remove co-purified proteins having molecular weights less than 50 kD from the Ni-NTA purified glycoprotein samples. The rhZP3 glycoprotein was found to be 80% pure, as judged by densitometry scanning of an electrophoresis gel of coomassie blue stained protein.

Experiment 7: Hemizona Assay ("HZA") of Sperm Biological Activity

Preparation of oocytes. Human immature (prophase I) oocytes were stored in a hyperosmotic solution containing 1.5M $MgCl_2$ supplemented with 40 mM Hepes buffer at pH 7.3 and 0.1% polyvinylpyrrolidone. Oocytes could be stored for up to 90 days at 4° C. without affecting performance of the HZA assay. Prior to cutting, oocytes were washed in a culture medium of Ham's F-10 (Gibco Laboratories, Grand Island, N.Y.). Narishige micromanipulators (Tokyo, Japan) mounted on a phase-contrast inverted microscope (Nikon Diaphot, Garden City, N.Y.) were utilized to cut each oocyte into two halves, termed hemizonae.

Preparation of sperm and exposure to 30 ng/ml rhZP3. An aliquot of semen was washed with 2 volumes of Ham's F-10 supplemented with 5% human serum albumin ("HSA"). The sperm suspension was centrifuged for 8 minutes at 400×g. This wash was repeated. The final pellet was overlaid with 500 ul of Ham's F-10/5% HSA and incubated for one hour in the presence of 5% $CO_2$ at 37° C. The HSA sperm suspension then was removed and divided into two portions. One portion was used as control sperm (4 hours at 5% $CO_2$, 37° C.). The second portion was incubated under identical conditions but in the presence of 30 ng/ml rhZP3. Supernatants containing motile spermatozoa were removed and a 100 ul droplet of each was separately placed into a petri dish submerged in mineral oil.

Incubation of sperm with hemizonae. One hemizona was transferred to the control droplet and its corresponding hemizona was placed into the rhZP3 treated droplet. Gametes were incubated for 4 hours at 5% $CO_2$, 37° C. The hemizonae then were rinsed in culture medium, using a finely drawn glass pipette to dislodge loosely attached sperm.

Results. The number of spermatozoa tightly bound to the convex surface of each hemizona was visually determined with a phase-contrast microscope at 200× magnification. For each sample, a "hemizona index" was calculated as the percentile ratio of the number of rhZP3-treated sperm bound to the number of non-treated control sperm bound. Defective sperm from infertile patients will generate a lower hemizona index than normal sperm and can be clinically detected this way.

Experiment 8: Immunofluorescence Assay of Acrosome Reaction

Semen was obtained from normal donors and allowed to liquefy for 30–60 minutes at room temperature. Semen was divided into 0.5 ml aliquots that were placed at the bottom of plastic 15 ml tubes. Each aliquot was washed with 2 volumes of Ham's F-10 (Sigma) supplemented with 5% human serum albumin. The sperm suspension was centrifuged for 8 minutes at 400×g. This wash was repeated one. The final pellet was overlaid with 500 ml of Ham's F-10 with 5% human serum albumin. The tubes are loosely capped and incubated at a 30° angle for one hour at 37° C. in 5% carbon dioxide, allowing sperm to swim from semen into the medium.

A probe of fluorescein isothiocyanate-conjugated *Pisum Satvum* agglutinin (PSA, Vector Lab, Burlingame, Calif.) was used to evaluate the acrosomal status of spermatozoa in spot slides. The same slides were counterstained with Hoescht stain, a DNA-specific stain that enters the nuclear membrane of dead spermatozoa, giving a fluorescent counterstain. An epifluorescent microscope was used to read the spot slides at a power of 400× magnification. Triplicate slides were made for the assay. At least 100 cells were evaluated per spot slide within the grid of the eyepiece of the microscope from 10 random fields. Two trained researchers were assigned to read the results, which were averaged. The results were expressed as percentiles of acrosome-reacted spermatozoa in the total population counted. Spermatozoa that had been treated with cell culture medium from Experiment 4 that contained hZP3 formed significantly more acrosome reactions compared to spermatozoa that had been treatment with a control (no hZP3 protein) medium.

All of the publications (including internet web site) and issued patents cited herein are explicitly incorporated in their entireties by reference.

TABLE 1

| Position No. | Preferred Amino Acid | Other Representative Amino Acids |
| --- | --- | --- |
| 310 | phe | tyr |
| 315 | pro | |
| 320 | gln | asp |
| 323 | asn | gln |
| 324 | lys | |
| 326 | asp | asn, glu, gln, ile, pro, phe, cys |
| 328 | gly | ala, ile |
| 329 | thr | ser |
| 330 | pro | |
| 332 | his | lys |
| 334 | arg | lys |
| 335 | arg | lys |
| 337 | pro | met |
| 339 | val | iso, met |
| 341 | ser | thr |
| 342 | gln | asn |
| 345 | arg | lys |

We claim:

1. A recombinantly produced polypeptide expressed by a human ovarian cell line, consisting essentially of the amino acid sequence of SEQ ID No: 2, wherein said polypeptide binds human spermatozoa.

2. A recombinantly produced glycopolypeptide expressed by a human ovarian cell line, consisting essentially of the amino acid sequence of SEQ ID No: 2.

3. A recombinantly produced polypeptide expressed by a human ovarian cell line, consisting essentially of the amino acid sequence of SEQ ID No: 2, or a conservatively substituted amino acid sequence thereof, said conservative substitutions being at least one of the amino acid residue numbers; 3, 8, 13, 16, 17, 19, 21, 22, 23, 25, 27, 28, 30, 32, 33, 34, 35, 38 and 39 according to SEQ ID No: 2, wherein said polypeptide binds human spermatozoa at least ten times as strong as an equivalent molar amount of mouse ZP3.

4. A recombinantly produced glycopolypeptide expressed by a human ovarian cell line, consisting essentially of the amino acid sequence of SEQ ID No: 2, or a conservatively substituted amino acid sequence thereof, said conservative substitutions being at least one of the amino acid residue numbers; 3, 8, 13, 16, 17, 19, 21, 22, 23, 25, 27, 28, 30, 32, 33, 34, 35, 38 and 39 according to SEQ ID NO: 2, wherein said glycopolypeptide binds human spermatozoa at least ten times as strong as an equivalent molar amount of mouse ZP3.

5. A recombinantly produced polypeptide according to claim 3, wherein the conserved amino acid substitutions at the following positions of SEQ ID No: 2 are as follows:

3 is selected from the group consisting of Phe and Tyr;
13 is selected from the group consisting of Gln and Asp;
16 is selected from the group consisting of Asn and Gln;
19 is selected from the group consisting of Asp, Asn, Glu, Gln, Ile, Pro, Phe and Cys;
21 is selected from the group consisting of Gly, Ala and Ile;
22 is selected from the group consisting of of Thr and Ser;
25 is selected from the group consisting of His and Lys;
27 is selected from the group consisting of Arg and Lys;
28 is selected from the group consisting of Arg and Lys;
30 is selected from the group consisting of Pro and Met;
32 is selected from the group consisting of Val, Ile and Met;
34 is selected from the group consisting of Ser and Thr;
35 is selected from the group consisting of Gln and Asn; and
38 is selected from the group consisting of Arg and Lys.

6. A recombinantly produced glycopolypeptide according to claim 4, wherein the conserved amino acid substitutions at the following positions of SEQ ID No: 2 are as follows:

3 is selected from the group consisting of Phe and Tyr;
13 is selected from the group consisting of Gln and Asp;
16 is selected from the group consisting of Asn and Gln;
19 is selected from the group consisting of Asp, Asn, Glu, Gln, Ile, Pro, Phe and Cys;
21 is selected from the group consisting of Gly, Ala and Ile;
22 is selected from the group consisting of of Thr and Ser;

25 is selected from the group consisting of His and Lys;
27 is selected from the group consisting of Arg and Lys;
28 is selected from the group consisting of Arg and Lys;
30 is selected from the group consisting of Pro and Met;
32 is selected from the group consisting of Val, Ile and Met;
34 is selected from the group consisting of Ser and Thr
35 is selected from the group consisting of Gln and Asn; and
38 is selected from the group consisting of Arg and Lys.

7. A glycosolated recombinant human zona pellucida protein 3 expressed by a human ovarian cell line having sperm-binding and acrosome reaction inducing activity, consisting of SEQ ID No: 2.

8. The protein of claim 7, wherein the ovarian cell line is selected from the group consisting of PA-1, $EB_2$, CaoV-3, OVCAR-3, SKOV-3 and SW626.

9. The protein of claim 7, wherein the ovarian cell line is PA-1.

* * * * *

SEQUENCE LISTING

<160> NUMBER OF SEQ ID NOS: 5

<210> SEQ ID NO 1
<211> LENGTH: 41
<212> TYPE: PRT
<213> ORGANISM: Homo sapiens

<400> SEQUENCE: 1

Ser Trp Phe Pro Val Glu Gly Pro Ala Asp Ile Cys Gln Cys Cys Asn
 1               5                  10                  15

Lys Gly Asp Cys Gly Thr Pro Ser His Ser Arg Arg Gln Pro His Val
            20                  25                  30

Met Ser Gln Trp Ser Arg Ser Ala Ser
         35                  40

<210> SEQ ID NO 2
<211> LENGTH: 41
<212> TYPE: PRT
<213> ORGANISM: Homo sapiens

<400> SEQUENCE: 2

Ser Trp Phe Pro Val Glu Gly Pro Ala Asp Ile Cys Gln Cys Cys Asn
 1               5                  10                  15

Lys Gly Asp Cys Gly Thr Pro Ser His Ser Arg Arg Gln Pro His Val
            20                  25                  30

Met Ser Gln Trp Ser Arg Ser Ala Ser
         35                  40

<210> SEQ ID NO 3
<211> LENGTH: 41

-continued

```
<212> TYPE: PRT
<213> ORGANISM: Mouse

<400> SEQUENCE: 3

Ser Trp Leu Pro Val Gln Gly Asp Ala Asp Ile Cys Asp Cys Cys Ser
 1               5                  10                  15

His Gly Asn Cys Ser Asn Ser Ser Ser Gln Phe Gln Ile His Gly
             20                  25                  30

Pro Arg Gln Trp Ser Lys Leu Val Ser
         35                  40

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
accatggagc tgagctatag g                                              21

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: Primer

<400> SEQUENCE: 5
ttctcgagtt aatgatgatg atgatgatga tgatcggaag cagacacaca gggtgggagg    60
cagt                                                                 64
```